United States Patent
Allavatam et al.

(10) Patent No.: US 8,626,280 B2
(45) Date of Patent: Jan. 7, 2014

(54) METHODS AND DEVICES FOR ACCURATELY CLASSIFYING CARDIAC ACTIVITY

(75) Inventors: Venugopal Allavatam, Oceanside, CA (US); Surekha Palreddy, Maplewood, MN (US); Rick Sanghera, San Clemente, CA (US); Jay A. Warren, San Juan Capistrano, CA (US)

(73) Assignee: Cameron Health, Inc., San Clemente, CA (US)

( * ) Notice: Subject to any disclaimer, the term of this patent is extended or adjusted under 35 U.S.C. 154(b) by 0 days.

(21) Appl. No.: 13/436,398

(22) Filed: Mar. 30, 2012

(65) Prior Publication Data
US 2012/0197147 A1    Aug. 2, 2012

Related U.S. Application Data

(62) Division of application No. 12/399,914, filed on Mar. 6, 2009, now Pat. No. 8,160,686.

(60) Provisional application No. 61/051,332, filed on May 7, 2008, provisional application No. 61/034,938, filed on Mar. 7, 2008.

(51) Int. Cl.
    *A61B 5/0468*    (2006.01)
(52) U.S. Cl.
    USPC ............................................. 600/516
(58) Field of Classification Search
    USPC ............................................. 600/516
    See application file for complete search history.

(56) References Cited

U.S. PATENT DOCUMENTS

| | | |
|---|---|---|
| 4,184,493 A | 1/1980 | Langer et al. |
| 4,300,567 A | 11/1981 | Kolenik et al. |
| 4,407,288 A | 10/1983 | Langer et al. |
| 4,450,527 A | 5/1984 | Sramek |
| 4,457,315 A | 7/1984 | Bennish |
| 4,589,420 A | 5/1986 | Adams et al. |
| 4,595,009 A | 6/1986 | Leinders |
| 4,679,144 A | 7/1987 | Cox et al. |
| 4,693,253 A | 9/1987 | Adams |

(Continued)

FOREIGN PATENT DOCUMENTS

| | | |
|---|---|---|
| CN | 1819855 A | 8/2006 |
| CN | 1829554 A | 9/2006 |

(Continued)

OTHER PUBLICATIONS

"U.S. Appl. No. 12/399,901, Final Office Action mailed Apr. 11, 2013", 11 pgs.

(Continued)

*Primary Examiner* — Eric D. Bertram
(74) *Attorney, Agent, or Firm* — Schwegman Lundberg & Woessner, P.A.

(57) ABSTRACT

Methods, systems, and devices for signal analysis in an implanted cardiac monitoring and treatment device such as an implantable cardioverter defibrillator. In illustrative examples, captured data including detected events is analyzed to identify likely overdetection of cardiac events. In some illustrative examples, when overdetection is identified, data may be modified to correct for overdetection, to reduce the impact of overdetection, or to ignore overdetected data. New methods for organizing the use of morphology and rate analysis in an overall architecture for rhythm classification and cardiac signal analysis are also discussed.

20 Claims, 26 Drawing Sheets

(56) References Cited

U.S. PATENT DOCUMENTS

| | | |
|---|---|---|
| 4,750,494 A | 6/1988 | King |
| 4,779,617 A | 10/1988 | Whigham |
| 4,940,054 A | 7/1990 | Grevis et al. |
| 4,979,110 A | 12/1990 | Albrecht et al. |
| 4,989,602 A | 2/1991 | Sholder et al. |
| 5,000,189 A | 3/1991 | Throne et al. |
| 5,105,810 A | 4/1992 | Collins et al. |
| 5,117,824 A | 6/1992 | Keimel et al. |
| 5,184,616 A | 2/1993 | Weiss |
| 5,193,535 A | 3/1993 | Bardy et al. |
| 5,215,098 A | 6/1993 | Steinhaus et al. |
| 5,217,021 A | 6/1993 | Steinhaus et al. |
| 5,240,009 A | 8/1993 | Williams |
| 5,271,411 A | 12/1993 | Ripley et al. |
| 5,273,049 A | 12/1993 | Steinhaus et al. |
| 5,280,792 A | 1/1994 | Leong et al. |
| 5,299,119 A | 3/1994 | Kraf et al. |
| 5,313,953 A | 5/1994 | Yomtov et al. |
| 5,331,966 A | 7/1994 | Bennett et al. |
| 5,339,820 A | 8/1994 | Henry et al. |
| 5,342,402 A | 8/1994 | Olson et al. |
| 5,342,407 A | 8/1994 | Dahl et al. |
| 5,351,696 A | 10/1994 | Riff et al. |
| 5,376,104 A | 12/1994 | Sakai et al. |
| 5,400,795 A | 3/1995 | Murphy et al. |
| 5,423,326 A | 6/1995 | Wang et al. |
| 5,447,519 A | 9/1995 | Peterson |
| 5,464,431 A | 11/1995 | Adams et al. |
| 5,470,342 A | 11/1995 | Mann et al. |
| 5,486,199 A | 1/1996 | Kim et al. |
| 5,513,644 A | 5/1996 | McClure et al. |
| 5,522,852 A | 6/1996 | White et al. |
| 5,534,019 A | 7/1996 | Paspa |
| 5,545,186 A | 8/1996 | Olson et al. |
| 5,558,098 A | 9/1996 | Fain |
| 5,564,430 A | 10/1996 | Jacobson et al. |
| 5,607,455 A | 3/1997 | Armstrong |
| 5,620,466 A | 4/1997 | Haefner et al. |
| 5,658,317 A | 8/1997 | Haefner et al. |
| 5,676,690 A | 10/1997 | Noren |
| 5,685,315 A | 11/1997 | McClure et al. |
| 5,702,425 A | 12/1997 | Wickham |
| 5,709,215 A | 1/1998 | Perttu et al. |
| 5,755,738 A | 5/1998 | Kim et al. |
| 5,776,168 A | 7/1998 | Gunderson |
| 5,779,645 A | 7/1998 | Olson et al. |
| 5,817,134 A | 10/1998 | Greenhut et al. |
| 5,827,197 A | 10/1998 | Bocek et al. |
| 5,857,977 A | 1/1999 | Caswell et al. |
| 5,891,048 A | 4/1999 | Nigam et al. |
| 5,991,657 A | 11/1999 | Kim |
| 6,029,086 A | 2/2000 | Kim et al. |
| 6,041,251 A | 3/2000 | Kim et al. |
| 6,047,210 A | 4/2000 | Kim et al. |
| 6,052,617 A | 4/2000 | Kim |
| 6,058,328 A | 5/2000 | Levine et al. |
| 6,095,987 A | 8/2000 | Shmulewitz et al. |
| 6,115,628 A | 9/2000 | Stadler et al. |
| 6,144,879 A | 11/2000 | Gray |
| 6,148,230 A | 11/2000 | Kenknight |
| 6,223,078 B1 | 4/2001 | Marcovecchio |
| 6,230,055 B1 | 5/2001 | Sun et al. |
| 6,236,882 B1 | 5/2001 | Lee et al. |
| 6,240,313 B1 | 5/2001 | Esler |
| 6,266,554 B1 | 7/2001 | Hsu et al. |
| 6,280,462 B1 | 8/2001 | Hauser et al. |
| 6,308,095 B1 | 10/2001 | Hsu et al. |
| 6,334,071 B1 | 12/2001 | Lu |
| 6,377,844 B1 | 4/2002 | Graen et al. |
| 6,381,493 B1 | 4/2002 | Stadler et al. |
| 6,393,316 B1 | 5/2002 | Gillberg et al. |
| 6,397,100 B2 | 5/2002 | Stadler et al. |
| 6,411,844 B1 | 6/2002 | Kroll et al. |
| 6,438,410 B2 | 8/2002 | Hsu et al. |
| 6,449,503 B1 | 9/2002 | Hsu |
| 6,493,579 B1 | 12/2002 | Gilkerson et al. |
| 6,493,584 B1 | 12/2002 | Lu |
| 6,505,068 B2 | 1/2003 | Bonnet et al. |
| 6,516,225 B1 | 2/2003 | Florio |
| 6,561,984 B1 | 5/2003 | Turcott |
| 6,567,691 B1 | 5/2003 | Stadler |
| 6,574,505 B1 | 6/2003 | Warren |
| 6,575,912 B1 | 6/2003 | Turcott |
| 6,587,720 B2 | 7/2003 | Hsu et al. |
| 6,625,490 B1 | 9/2003 | McClure et al. |
| 6,643,549 B1 | 11/2003 | Bradley et al. |
| 6,647,292 B1 | 11/2003 | Bardy et al. |
| 6,684,100 B1 | 1/2004 | Sweeney et al. |
| 6,699,200 B2 | 3/2004 | Cao et al. |
| 6,708,058 B2 | 3/2004 | Kim et al. |
| 6,708,062 B2 | 3/2004 | Ericksen et al. |
| 6,721,597 B1 | 4/2004 | Bardy et al. |
| 6,728,572 B2 | 4/2004 | Hsu et al. |
| 6,731,978 B2 | 5/2004 | Olson et al. |
| 6,745,068 B2 | 6/2004 | Koyrakh et al. |
| 6,754,528 B2 | 6/2004 | Bardy et al. |
| 6,889,079 B2 | 5/2005 | Bocek et al. |
| 6,892,092 B2 | 5/2005 | Palreddy et al. |
| 6,909,916 B2 | 6/2005 | Spinelli et al. |
| 6,950,702 B2 | 9/2005 | Sweeney |
| 7,016,730 B2 | 3/2006 | Ternes |
| 7,020,523 B1 | 3/2006 | Lu et al. |
| 7,027,856 B2 | 4/2006 | Zhou et al. |
| 7,027,858 B2 | 4/2006 | Cao et al. |
| 7,027,862 B2 | 4/2006 | Dahl et al. |
| 7,031,764 B2 | 4/2006 | Schwartz et al. |
| 7,062,314 B2 | 6/2006 | Zhu et al. |
| 7,062,315 B2 | 6/2006 | Koyrakh et al. |
| 7,062,322 B2 | 6/2006 | Stadler et al. |
| 7,076,289 B2 | 7/2006 | Sarkar et al. |
| 7,085,599 B2 | 8/2006 | Kim et al. |
| 7,103,412 B1 | 9/2006 | Kroll |
| 7,117,035 B2 | 10/2006 | Wagner et al. |
| 7,123,954 B2 | 10/2006 | Narayan et al. |
| 7,149,575 B2 | 12/2006 | Ostroff et al. |
| 7,162,301 B2 | 1/2007 | Kim et al. |
| 7,167,747 B2 | 1/2007 | Gunderson et al. |
| 7,184,815 B2 | 2/2007 | Kim et al. |
| 7,184,818 B2 | 2/2007 | Kim et al. |
| 7,191,004 B2 | 3/2007 | Kim et al. |
| 7,194,302 B2 | 3/2007 | Bardy et al. |
| 7,218,966 B2 | 5/2007 | Haefner |
| 7,236,819 B2 | 6/2007 | Brockway et al. |
| 7,248,921 B2 | 7/2007 | Palreddy et al. |
| 7,266,409 B2 | 9/2007 | Gunderson |
| 7,283,863 B2 | 10/2007 | Gunderson et al. |
| 7,302,294 B2 | 11/2007 | Kamath et al. |
| 7,330,757 B2 | 2/2008 | Ostroff et al. |
| 7,346,392 B2 | 3/2008 | Kenknight |
| 7,376,458 B2 | 5/2008 | Palreddy et al. |
| 7,379,772 B2 | 5/2008 | Bardy et al. |
| 7,386,342 B1 | 6/2008 | Falkenberg et al. |
| 7,392,085 B2 | 6/2008 | Warren et al. |
| 7,444,182 B2 | 10/2008 | Ostroff et al. |
| 7,447,540 B1 | 11/2008 | Nabutovsky et al. |
| 7,467,009 B2 | 12/2008 | Palreddy et al. |
| 7,477,935 B2 | 1/2009 | Palreddy et al. |
| 7,496,408 B2 | 2/2009 | Ghanem et al. |
| 7,496,409 B2 | 2/2009 | Greenhut et al. |
| 7,499,750 B2 | 3/2009 | Haefner et al. |
| 7,522,959 B2 | 4/2009 | Hauser et al. |
| 7,546,159 B1 | 6/2009 | Nabutovsky et al. |
| 7,555,335 B2 | 6/2009 | Kamath et al. |
| 7,559,900 B2 | 7/2009 | Gillberg |
| 7,567,835 B2 | 7/2009 | Gunderson et al. |
| 7,570,997 B2 | 8/2009 | Lovett et al. |
| 7,593,771 B2 | 9/2009 | Yonce et al. |
| 7,623,913 B2 | 11/2009 | Phillips |
| 7,623,916 B2 | 11/2009 | Julian |
| 7,655,014 B2 | 2/2010 | Ko et al. |
| 7,682,316 B2 | 3/2010 | Anderson et al. |
| 7,684,864 B2 | 3/2010 | Olson et al. |
| 7,715,906 B2 | 5/2010 | Krause et al. |
| 7,734,345 B2 | 6/2010 | Cinbis |

(56) References Cited

U.S. PATENT DOCUMENTS

| | | | |
|---|---|---|---|
| 7,761,142 B2 | 7/2010 | Ghanem et al. | |
| 7,774,049 B2 * | 8/2010 | Ghanem et al. | 600/509 |
| 7,783,354 B2 | 8/2010 | Gunderson | |
| 7,792,571 B2 | 9/2010 | Sweeney et al. | |
| 7,797,036 B2 | 9/2010 | Zhang et al. | |
| 7,801,594 B1 | 9/2010 | Higham | |
| 7,865,233 B2 | 1/2011 | Haefner | |
| 7,894,894 B2 | 2/2011 | Stadler et al. | |
| 7,904,142 B2 | 3/2011 | Kim et al. | |
| 7,904,153 B2 | 3/2011 | Greenhut et al. | |
| 7,907,993 B2 | 3/2011 | Ghanem et al. | |
| 2003/0204215 A1 | 10/2003 | Gunderson et al. | |
| 2004/0049120 A1 | 3/2004 | Cao et al. | |
| 2004/0215239 A1 | 10/2004 | Favet et al. | |
| 2004/0215240 A1 | 10/2004 | Lovett et al. | |
| 2004/0220628 A1 | 11/2004 | Wagner | |
| 2004/0230229 A1 | 11/2004 | Lovett et al. | |
| 2005/0107838 A1 | 5/2005 | Lovett et al. | |
| 2005/0131464 A1 | 6/2005 | Heinrich et al. | |
| 2005/0154421 A1 | 7/2005 | Ousdigian et al. | |
| 2006/0116595 A1 | 6/2006 | Palreddy et al. | |
| 2006/0116725 A1 | 6/2006 | Palreddy et al. | |
| 2006/0122676 A1 | 6/2006 | Ko | |
| 2006/0167502 A1 | 7/2006 | Haefner | |
| 2006/0167503 A1 | 7/2006 | Warren et al. | |
| 2006/0167504 A1 | 7/2006 | Warren et al. | |
| 2006/0235476 A1 | 10/2006 | Gunderson | |
| 2006/0241701 A1 | 10/2006 | Markowitz et al. | |
| 2007/0032829 A1 | 2/2007 | Ostroff | |
| 2007/0049975 A1 | 3/2007 | Cates et al. | |
| 2007/0135847 A1 | 6/2007 | Kenknight | |
| 2007/0142736 A1 | 6/2007 | Cazares et al. | |
| 2007/0156190 A1 | 7/2007 | Cinbis | |
| 2007/0179539 A1 | 8/2007 | Degroot et al. | |
| 2007/0179540 A1 | 8/2007 | Stegemann et al. | |
| 2007/0232944 A1 | 10/2007 | Ghanem et al. | |
| 2007/0232945 A1 | 10/2007 | Kleckner et al. | |
| 2007/0232948 A1 | 10/2007 | Stadler et al. | |
| 2007/0233198 A1 | 10/2007 | Ghanem et al. | |
| 2007/0276445 A1 | 11/2007 | Sanghera et al. | |
| 2008/0015647 A1 | 1/2008 | Palreddy et al. | |
| 2008/0077030 A1 | 3/2008 | Ostroff | |
| 2008/0086174 A1 | 4/2008 | Libbus et al. | |
| 2008/0091242 A1 | 4/2008 | Kamath et al. | |
| 2008/0132965 A1 | 6/2008 | Ostroff | |
| 2008/0161870 A1 | 7/2008 | Gunderson | |
| 2008/0172098 A1 | 7/2008 | Gunderson et al. | |
| 2008/0183085 A1 | 7/2008 | Van Oort et al. | |
| 2008/0188901 A1 | 8/2008 | Sanghera et al. | |
| 2008/0215110 A1 | 9/2008 | Gunderson | |
| 2008/0221632 A1 | 9/2008 | Bardy et al. | |
| 2008/0228093 A1 | 9/2008 | Dong et al. | |
| 2008/0243200 A1 | 10/2008 | Scinicariello et al. | |
| 2008/0262559 A1 | 10/2008 | Zhang et al. | |
| 2008/0275516 A1 | 11/2008 | Ghanem et al. | |
| 2008/0275517 A1 | 11/2008 | Ghanem et al. | |
| 2008/0275519 A1 | 11/2008 | Ghanem et al. | |
| 2008/0275521 A1 | 11/2008 | Warren et al. | |
| 2008/0288009 A1 | 11/2008 | Kim et al. | |
| 2009/0036788 A1 | 2/2009 | Nabutovsky et al. | |
| 2009/0043352 A1 | 2/2009 | Brooke et al. | |
| 2009/0054796 A1 | 2/2009 | Sanghera et al. | |
| 2009/0054938 A1 | 2/2009 | Ostroff et al. | |
| 2009/0093731 A1 | 4/2009 | Palreddy et al. | |
| 2009/0156957 A1 | 6/2009 | Linder et al. | |
| 2009/0157128 A1 | 6/2009 | Seim et al. | |
| 2009/0157132 A1 | 6/2009 | Linder et al. | |
| 2009/0157137 A1 | 6/2009 | Gilkerson et al. | |
| 2009/0187227 A1 | 7/2009 | Palreddy et al. | |
| 2009/0228057 A1 | 9/2009 | Allavatam et al. | |
| 2009/0240157 A1 | 9/2009 | Lian et al. | |
| 2009/0240300 A1 | 9/2009 | Lian et al. | |
| 2009/0259271 A1 | 10/2009 | Allavatam et al. | |
| 2010/0004713 A1 | 1/2010 | Warren et al. | |
| 2010/0094369 A1 | 4/2010 | Allavatam et al. | |
| 2010/0152798 A1 | 6/2010 | Sanghera et al. | |
| 2010/0152799 A1 | 6/2010 | Sanghera et al. | |
| 2010/0185109 A1 | 7/2010 | Zhang et al. | |
| 2010/0331904 A1 | 12/2010 | Warren et al. | |
| 2011/0098585 A1 | 4/2011 | Warren et al. | |
| 2011/0098775 A1 | 4/2011 | Allavatam et al. | |
| 2013/0006085 A1 | 1/2013 | Allavatam et al. | |

FOREIGN PATENT DOCUMENTS

| | | |
|---|---|---|
| CN | 1915166 A | 2/2007 |
| CN | 1985750 A | 6/2007 |
| CN | 101065059 A | 10/2007 |
| EP | 0554208 A2 | 8/1993 |
| WO | WO-2004105871 A1 | 12/2004 |
| WO | WO-2009111764 A2 | 9/2009 |
| WO | WO-2009111764 A3 | 9/2009 |
| WO | WO-2009111766 A2 | 9/2009 |
| WO | WO-2009111766 A3 | 9/2009 |
| WO | WO-2009137726 A2 | 11/2009 |
| WO | WO-2009137726 A3 | 11/2009 |

OTHER PUBLICATIONS

"U.S. Appl. No. 12/399,901, Non Final Office Action mailed Sep. 17, 2012", 44 pgs.

"U.S. Appl. No. 12/399,901, Response filed Apr. 6, 2012 to Restriction Requirement mailed Mar. 6, 2012", 25 pgs.

"U.S. Appl. No. 12/399,901, Response filed Dec. 17, 2012 to Non Final Office Action mailed Sep. 17, 2012", 16 pgs.

"U.S. Appl. No. 12/399,901, Restriction Requirement mailed Mar. 6, 2012", 8 pgs.

"U.S. Appl. No. 12/399,914, Non-Final Office Action mailed Oct. 21, 2011", 34 pgs.

"U.S. Appl. No. 12/399,914, Notice of Allowance mailed Feb. 14, 2012", 5 pgs.

"U.S. Appl. No. 12/399,914, Response filed Oct. 7, 2011 to Restriction Requirement mailed Sep. 9, 2011", 11 pgs.

"U.S. Appl. No. 12/399,914, Response received Jan. 13, 2012 to Non-Final Office Action mailed Oct. 21, 2011", 8 pgs.

"U.S. Appl. No. 12/399,914, Restriction Requirement mailed Sep. 9, 2011", 6 pgs.

"U.S. Appl. No. 12/437,547, Non-Final Office Action mailed Nov. 10, 2011", 34 pgs.

"U.S. Appl. No. 12/437,547, Notice of Allowance mailed Feb. 15, 2012", 5 pgs.

"U.S. Appl. No. 12/437,547, Response filed Jan. 27, 2012 to Non-Final Office Action mailed Nov. 10, 2011", 6 pgs.

"U.S. Appl. No. 12/437,547, Response filed Oct. 10, 2011 to Restriction Requirement mailed Sep. 9, 2011", 12 pgs.

"U.S. Appl. No. 12/437,547, Restriction Requirement mailed Sep. 9, 2011", 5 pgs.

"U.S. Appl. No. 12/637,438, Non-Final Office Action mailed Dec. 7, 2011", 34 pgs.

"U.S. Appl. No. 12/637,438, Notice of Allowance mailed May 16, 2012", 5 pgs.

"U.S. Appl. No. 12/637,438, Response filed Feb. 29, 2012 to Non-Final Office Action mailed Dec. 7, 2011", 11 pgs.

"U.S. Appl. No. 12/637,438, Response filed Nov. 18, 2011 to Restriction Requirement mailed Oct. 21, 2011", 8 pgs.

"U.S. Appl. No. 12/637,438, Restriction Requirement mailed Oct. 21, 2011", 7 pgs.

"U.S. Appl. No. 13/436,448, Non Final Office Action mailed Feb. 27, 2013", 6 pgs.

"U.S. Appl. No. 13/436,448, Response filed Feb. 13, 2013 to Restriction Requirement mailed Jan. 18, 2013", 9 pgs.

"U.S. Appl. No. 13/436,448, Restriction Requirement mailed Jan. 18, 2013", 6 pgs.

"U.S. Appl. No. 13/607,168, Non Final Office Action mailed Mar. 26, 2013", 7 pgs.

"U.S. Appl. No. 13/607,168, Response filed Mar. 14, 2013 to Restriction Requirement mailed Feb. 27, 2013", 6 pgs.

"U.S. Appl. No. 13/607,168, Restriction Requirement mailed Feb. 27, 2013", 5 pgs.

(56) References Cited

OTHER PUBLICATIONS

"Chinese Application Serial No. 200980116877.4, Office Action mailed Jan. 30, 2013", w/English translation, 17 pgs.
"Chinese Application Serial No. 200980116886.3, Office Action mailed Dec. 13, 2012", w/English Translation, 16 pgs.
"Chinese Application Serial No. 200980125869.6, Office Action mailed Jan. 10, 2013", (With English Translation), 12 pgs.
"European Application Serial No. 09717667.1, Office Action mailed Dec. 16, 2011", 4 pgs.
"European Application Serial No. 09717667.1, Response filed Apr. 26, 2012 to Office Action mailed Dec. 16, 2011", 44 pgs.
"European Application Serial No. 09717991.5, Office Action mailed Dec. 16, 2011", 4 pgs.
"European Application Serial No. 09717991.5, Response filed Apr. 26, 2012 to Office Action mailed Dec. 16, 2011", 41 pgs.
"European Application Serial No. 09743712.3, Office Action mailed Jun. 8, 2011", 3 pgs.
"European Application Serial No. 09743712.3, Response filed Aug. 10, 2011 to Office Action mailed Jun. 8, 2011", 9 pgs.
"European Application Serial No. 12151591.0, European Search Report mailed Mar. 21, 2012", 6 pgs.
"European Application Serial No. 12151591.0, Response filed Oct. 26, 2012 to European Search Report mailed Mar. 21, 2012", 10 pgs.
"European Application Serial No. 12151593.6, European Search Report mailed Mar. 21, 2012", 7 pgs.
"European Application Serial No. 12151593.6, Response filed Oct. 26, 2012 to European Search Report mailed Mar. 21, 2012", 13 pgs.
"European Application Serial No. 12151595.1, European Search Report mailed Mar. 21, 2012", 6 pgs.
"European Application Serial No. 12151595.1, Response filed Oct. 26, 2012 to European Search Report mailed Mar. 21, 2012", 9 pgs.
"European Application Serial No. 12189307.7, Extended European Search Report mailed Mar. 1, 2013", 6 pgs.
"European Application Serial No. 12189311.9, Extended European Search Report mailed Mar. 1, 2013", 6 pgs.
"International Application Serial No. PCT/US2009/036432, International Report on Patentability mailed Sep. 22, 2009".
"International Application Serial No. PCT/US2009/036432, International Search Report mailed Sep. 22, 2009", 5 pgs.
"International Application Serial No. PCT/US2009/036432, International Written Opinion mailed Sep. 7, 2010", 11 pgs.
"International Application Serial No. PCT/US2009/036434, International Preliminary Report on Patentability mailed Sep. 7, 2010", 14 pgs.
"International Application Serial No. PCT/US2009/036434, International Search Report mailed Sep. 22, 2009", 7 pgs.
"International Application Serial No. PCT/US2009/036434, International Written Opinion mailed Sep. 7, 2010", 13 pgs.
"International Application Serial No. PCT/US2009/043213, International Report on Patentability mailed Nov. 9, 2010", 13 pgs.
"International Application Serial No. PCT/US2009/043213, International Search Report mailed Dec. 1, 2009", 7 pgs.
"International Application Serial No. PCT/US2009/043213, International Written Opinion mailed Nov. 7, 2010", 12 pgs.
"Methods and Devices for Identifying and Correcting Overdetection of Cardiac Events", U.S. Appl. No. 61/051,332, filed May 7, 2008, 62 pgs.
"QT Interval", Wikipedia, [Online]. Retrieved from the Internet: <URL: http://en.wikipedia.org/wiki/QT_interval>, (Accessed May 11, 2011), 5 pgs.
Gunderson, et al., "An Algorithm to Predict Implantable Cardioverter-Defibrillator Lead Failure", JACC, vol. 44, No. 9, (Nov. 2004), 1898-902.
Olson, Walter, et al., "Onset and Stability for Ventricular Tachyarrhythmia Detection in an Implantable Pacer-Cardioverter-Defibrillator", IEEE, (1987), 167-170.
Schuder, John C, "The Role of an Engineering Oriented Medical Research Group in Developing Improved Methods & Devices for Achieving Ventricular Defibrillation: The University of Missouri Experience", PACE vol. 16, Part I, (Jan. 1993), 95-124.
Schwake, "Komplikationen mit Sonden bei 340 Patienten mit einem implantierbaren Kardioverter/Defibrilator", Z Kardiol 88, (1999), 559-565.
Swerdlow, C. D, et al., "Advanced ICD Troubleshooting: Part I.", accessed and printed Jul. 7, 2009, indicates publication Jan. 9, 2006 (publication date not confirmed)., [Online]. Retrieved from the Internet: <http://www.medscape.com/viewarticle/520588_print>, (Accessed Jul. 7, 2009), 1322-46.
Throne, Robert D, et al., "A Comparison of Four New Time-Domain Techniques for Discriminating Monomorphic Ventricular Tachycardia from Sinus Rhythm Using Ventricular Waveform Morphology", IEEE Transactions on Biomedical Engineering, vol. 38, No. 6, (Jun. 1991), 561-570.

* cited by examiner

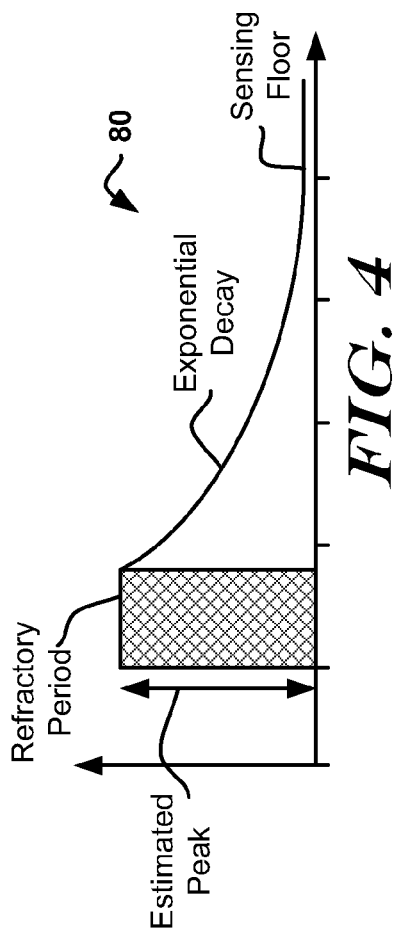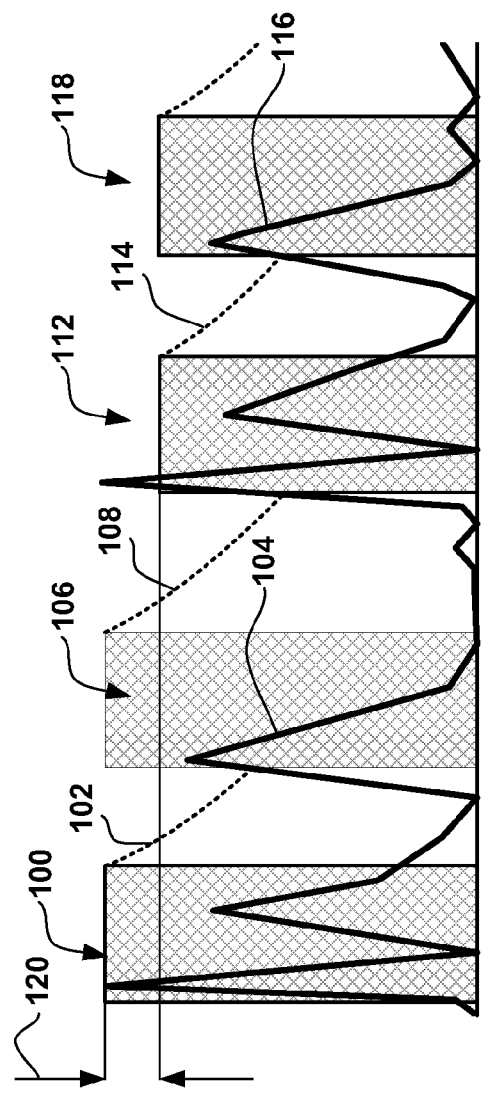

First Wide Complex Rule Set

322 Detection Interval Rule:
$t_1 <=$ Rule_1_Duration

326 AND

Peak Proximity Rule:
$t_2 <=$ Rule_2_Duration

| True False Marking 360 | | | | | |
|---|---|---|---|---|---|
| N-2 | N-1 | | N-2 | N-1 | |
| T | ? | Neither Rule Set Satisfied → | T | T | ← 362 |
| T | ? | Met Rules, Template Formed & CWA(n-2) ≤ CWA(n-1) → | F | T | ← 364 |
| T | ? | Met Rules, Any Other Score Combination or no template → | T | F | ← 366 |
| F | ? | Only result for n-2 = F → | F | T | ← 368 |

*FIG. 13A*

| Rate in Range, Pattern Found | | | | |
|---|---|---|---|---|
| N-3 | N-2 | N-1 | | 380 |
| T | F | T | Assign N-2 WC Overdetect Marker | 382 |
| Otherwise | | | No WC OD Marker Assigned | 384 |

| Rate in Range, No Pattern | | | | |
|---|---|---|---|---|
| N-3 | N-2 | N-1 | | 390 |
| T | F | T | Assign N-2 WC Suspect Event Marker | 392 |
| Otherwise | | | No WC Suspect Marker Assigned | 394 |

*FIG. 13B*

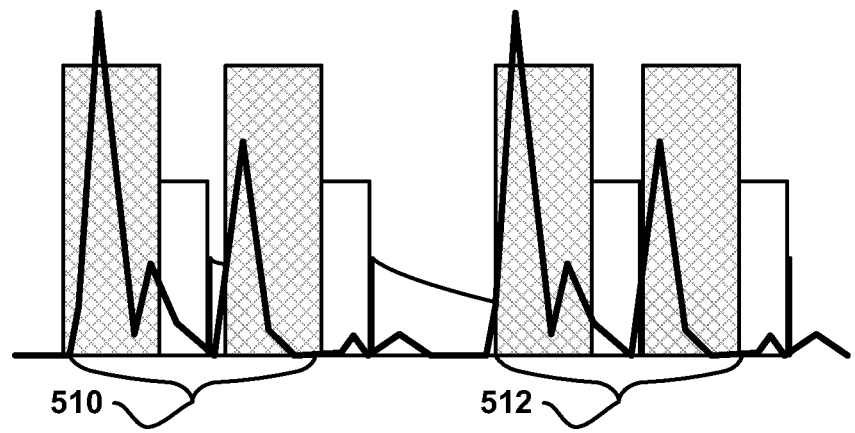
Overdetecting T-Waves
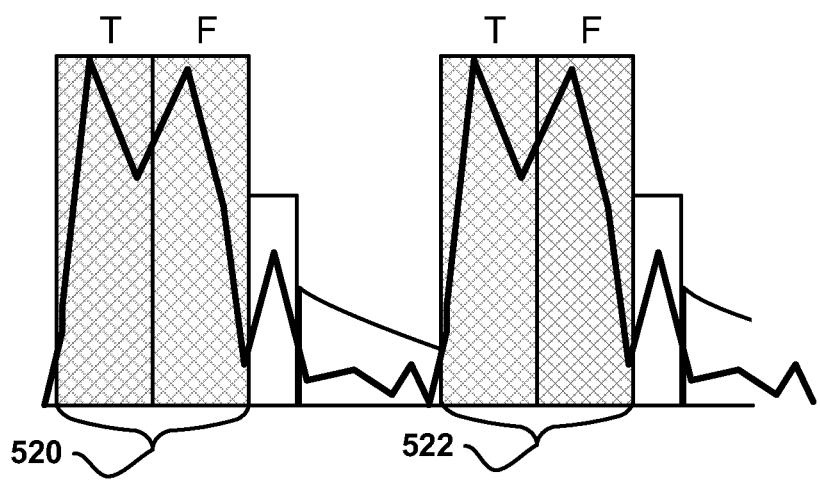
Overdetecting Wide Complexes
*FIG. 17*

METHODS AND DEVICES FOR ACCURATELY CLASSIFYING CARDIAC ACTIVITY

RELATED APPLICATIONS

The present application is a divisional of U.S. patent application Ser. No. 12/399,914, filed Mar. 6, 2009 and published as U.S. Patent Application Publication Number 2009-0259271, now issued as U.S. Pat. No. 8,160,686, which claims the benefit of and priority to U.S. Provisional Patent Application No. 61/051,332, filed May 7, 2008 and titled METHODS AND DEVICES FOR IDENTIFYING AND CORRECTING OVERDETECTION OF CARDIAC EVENTS, the disclosures of each of which are incorporated herein by reference; U.S. patent application Ser. No. 12/399,914, now issued as U.S. Pat. No. 8,160,686, also claims the benefit of and priority to U.S. Provisional Patent Application No. 61/034,938, filed Mar. 7, 2008 and titled ACCURATE CARDIAC EVENT DETECTION IN AN IMPLANTABLE CARDIAC STIMULUS DEVICE, the disclosure of which is incorporated herein by reference.

The present application is related to U.S. patent application Ser. No. 12/399,901, filed Mar. 6, 2009, published as U.S. Patent Application Publication Number 2009-0228057 and titled ACCURATE CARDIAC EVENT DETECTION IN AN IMPLANTABLE CARDIAC STIMULUS DEVICE, which claims the benefit of and priority to U.S. Provisional Patent Application No. 61/034,938, filed Mar. 7, 2008, and the disclosure of which is also incorporated herein by reference. The present application is also related to U.S. patent application Ser. No. 12/637,438, filed Dec. 14, 2009 and published as U.S. Patent Application Publication Number 2010-0094369, now issued as U.S. Pat. No. 8,265,749, which is a continuation of U.S. patent application Ser. No. 12/399,914, now issued as U.S. Pat. No. 8,160,686, claiming the benefit of and priority to U.S. 61/051,332 filed May 7, 2008 and U.S. 61/034,938 filed Mar. 7, 2008.

FIELD

The present invention relates generally to implantable medical device systems that sense and analyze cardiac signals. More particularly, the present invention relates to implantable medical devices that capture cardiac signals within an implantee's body in order to classify cardiac activity as likely benign or malignant.

BACKGROUND

Implantable cardiac devices typically sense cardiac electrical signals in an implantee and classify the implantee's cardiac rhythm as normal/benign or malignant. Illustrative malignant rhythms may include ventricular fibrillation and/or ventricular tachyarrhythmia. The accuracy with which an implantable medical device analyzes captured signals determines how well it makes therapy and other decisions.

New and/or alternative methods and devices for cardiac signal analysis are desired.

SUMMARY

Various illustrative embodiments of the present invention are directed toward improved accuracy in cardiac signal analysis by implantable medical devices. Some illustrative embodiments identify overdetection of cardiac events. Some illustrative embodiments also correct at least some captured data and use the corrected data to make operational decisions. The invention may be embodied in methods and/or devices.

BRIEF DESCRIPTION OF THE DRAWINGS

FIG. 4 is an illustration of a detection profile that may be used while detecting cardiac events in an implantable medical device;

FIG. 5 is a graphical illustration of double detection where both R and T waves are detected in each cardiac cycle;

FIGS. 13A-13B illustrate handling of outcomes from the rule set analysis of FIGS. 12A-12D;

FIG. 17 illustrates how modifications to the detection profile may fail to avoid overdetection in some circumstances;

DETAILED DESCRIPTION

The following detailed description should be read with reference to the drawings. The drawings, which are not necessarily to scale, depict illustrative embodiments and are not intended to limit the scope of the invention.

Some of the following examples and explanations include references to issued patents and pending patent applications. These references are for illustrative purposes and are not intended to limit the present invention to the particular methods or structures from those referenced patents and patent applications.

Unless implicitly required or explicitly stated, the methods below do not require any particular order of steps. It should be understood that when the following examples refer to a "current event," in some embodiments, this means the most recently detected cardiac event is being analyzed. However, this need not be the case, and some embodiments perform analysis that is delayed by one or more detections and or a fixed period of time.

Figure 6A:
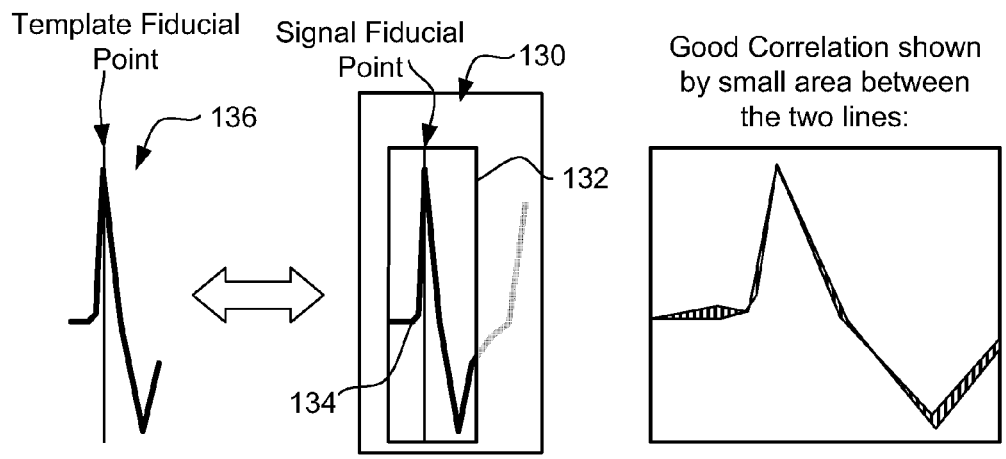
FIGS. 6A-6B show an illustrative method of morphological analysis of the detections in FIG. 5, relative to a stored R-wave template.
Figure 6B:
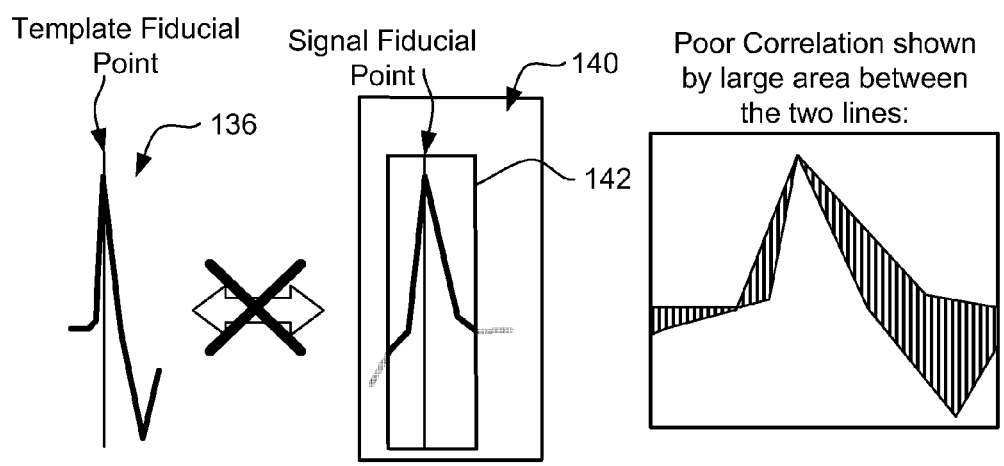
Figure 7A:
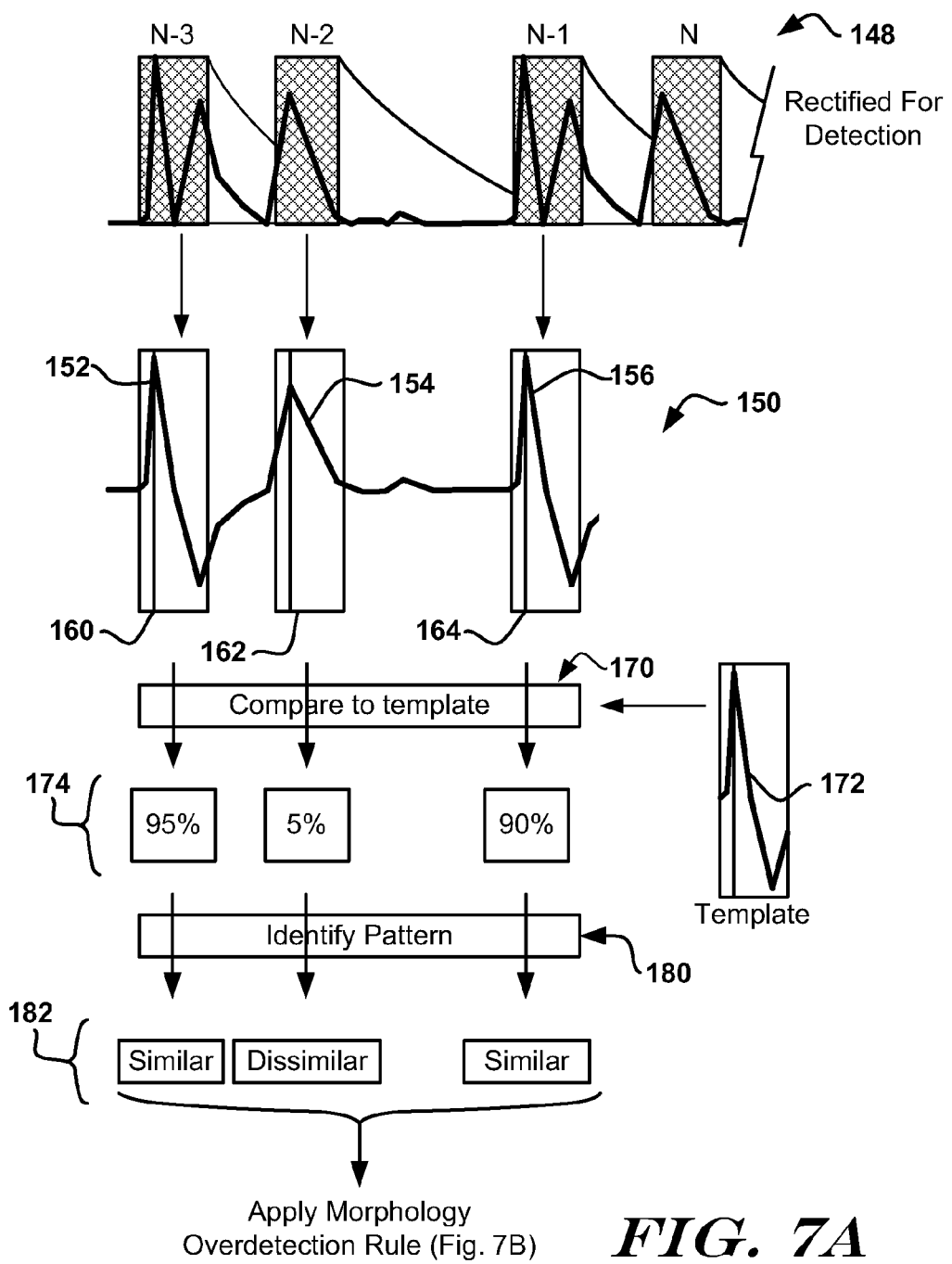
FIGS. 7A-7B provide a detailed example of illustrative identification of overdetections using morphology analysis.

The illustrative examples below use rectified captured signals for purposes of event detection, for example, as shown in FIGS. 5, 7A (at 148), 9, 11, 12C-12D, 17 and 18. Some illustrative examples perform analysis of shape characteristics (morphology) of the captured signals using an unrectified signal, as shown, for example, by FIGS. 6A-6B, 7A, 11 and 12A-12D. Choices shown regarding use of rectified/unrectified signals are merely illustrative, and may be changed if desired.

The nomenclature used herein indicates that a signal is sensed by an implantable cardiac device system, events are detected in the sensed signal, and cardiac activity is classified by use of the detected events (detections). Rhythm classification includes the identification of malignant rhythms, such as ventricular fibrillation or certain tachyarrhythmias, for example. Implantable therapy systems make therapy/stimulus decisions in reliance upon the classification of the cardiac rhythm.

In an illustrative example, a detected event is detected by comparing received signals to a detection threshold, which is defined by a detection profile. FIGS. 4 and 17, below, provide illustrative examples of detection profiles. Some embodiments of the present invention incorporate detection profiles and associated analysis as discussed in U.S. Provisional Patent Application No. 61/034,938, entitled ACCURATE CARDIAC EVENT DETECTION IN AN IMPLANTABLE CARDIAC STIMULUS DEVICE, filed on Mar. 7, 2008. Any suitable detection profile may be used.

Figure 18:
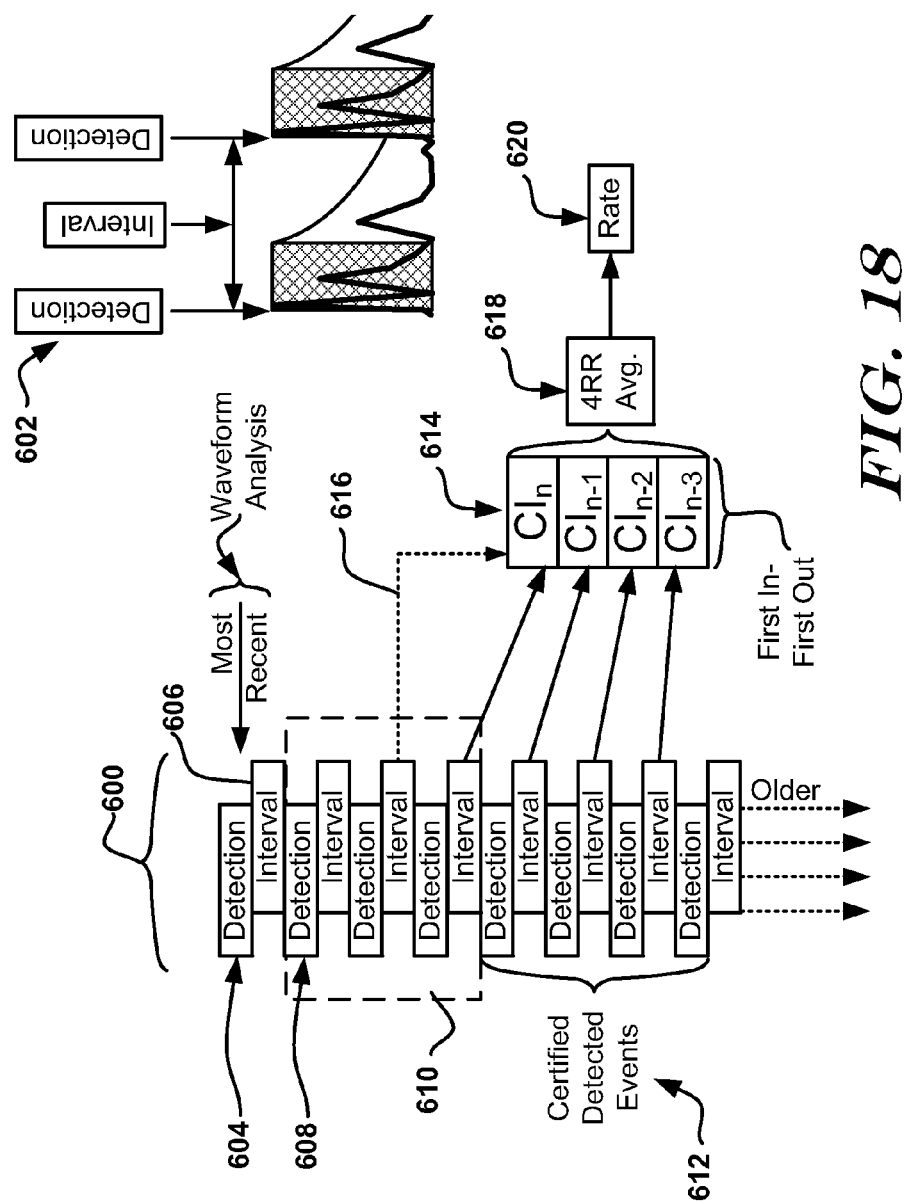
FIGS. 18-21 provide graphical illustrations of handling of suspect and overdetection markers in a stream of captured events.

Detected events are separated by intervals, for example, as shown in FIG. 18 at 602. Several intervals can be used to generate an average interval across a selected number of intervals. Some examples shown below use four intervals to calculate an average interval. Some other number of intervals may be used, as desired. The detected heart rate can then be calculated using the average interval.

A cardiac electrogram includes several portions (often referenced as "waves") that, according to well known convention, are labeled with letters including P, Q, R, S, and T, each of which corresponds to particular physiological events. It is typical to design detection algorithms to sense the R-wave, though any portion, if repeatedly detected, can be used to generate a beat rate. If morphology (shape) analysis is used in addition to heart rate, the system may capture and/or analyze the portion of the cycle that includes the Q, R and S waves, referred to as the QRS complex. Other portions of the patient's cardiac cycle, such as the P-wave and T-wave, are often treated as artifacts that are not sought for the purpose of estimating heart rate, though this need not be the case.

Typically, for purposes of ascertaining rate each cardiac cycle is counted only once. Overdetection (such as a double or triple detection) may occur if the device declares more than one detected event within a single cardiac cycle. FIGS. 5, 7A, 9, 11, 12C-12D and 17 each show, in one form or another, overdetection. Examples include the detection of both an R-wave and a trailing T-wave (see FIGS. 5, 7A, 9 and 17) as well as multiple detections of a wide QRS complex (see FIGS. 11, 12C-12D and 17). These examples are not intended to be exhaustive, and those skilled in the art understand that detection methods in implanted devices can be challenged by any number of variations of "normal" cardiac activity. For example, a P-wave may be detected and followed by detection of a trailing part of the QRS or a T-wave from the same cardiac cycle. Overdetection may also occur if noise causes an event to be declared when no cardiac event has taken place, for example, due to external therapy or noise, pacing artifact, skeletal muscle noise, electro-therapy, etc.

Overdetection can lead to overcounting of cardiac cycles. For example, if one cardiac cycle takes place and a detection algorithm declares multiple detected events, overdetection has occurred. If the heart rate is then calculated by counting each of these detections, overcounting occurs. Calculated heart rates may be used alone or in combination with other factors to classify cardiac rhythms as malignant or benign. Overcounting in reliance on overdetected events can result in erroneously high rate calculation. Miscalculation of heart rate can lead to incorrect rhythm classification and therapy decisions. Some embodiments are directed to identifying overdetection and/or correcting affiliated data.

Figure 1:
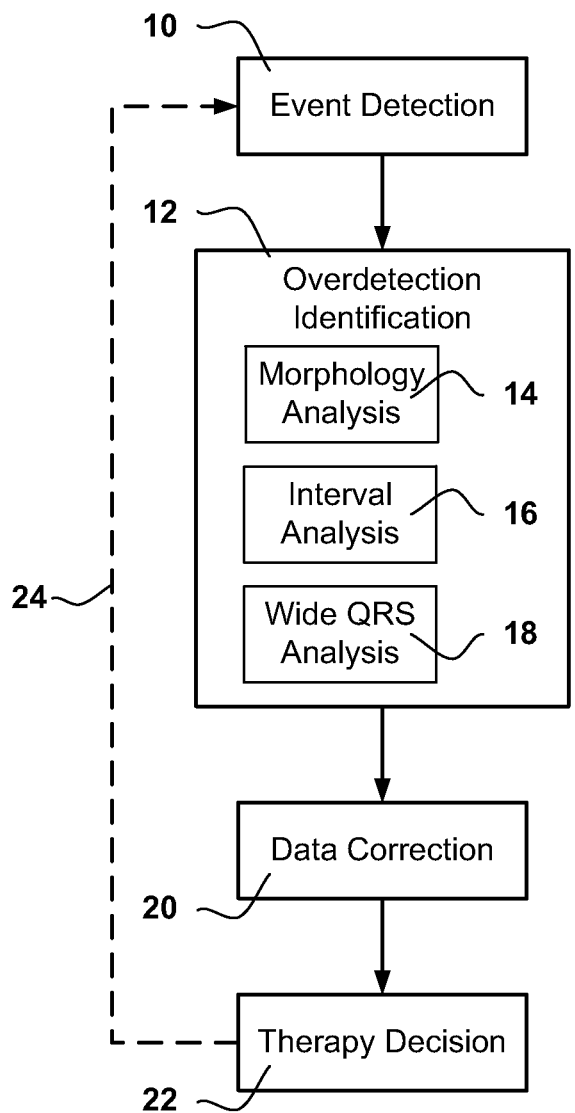
FIG. 1 is a block diagram for an illustrative method of identifying overdetection and taking corrective action.

FIG. 1 is a process flow diagram for an illustrative method of identifying overdetection and taking corrective action. The illustrative method begins with event detection 10, where the received cardiac signal is captured and compared to a detection threshold until the received signal crosses the detection threshold, resulting in declaration of a detected event. FIGS. 4-5 provide illustration of detection step 10. An additional detection profile example is shown in FIG. 17 as well.

Figure 7B:
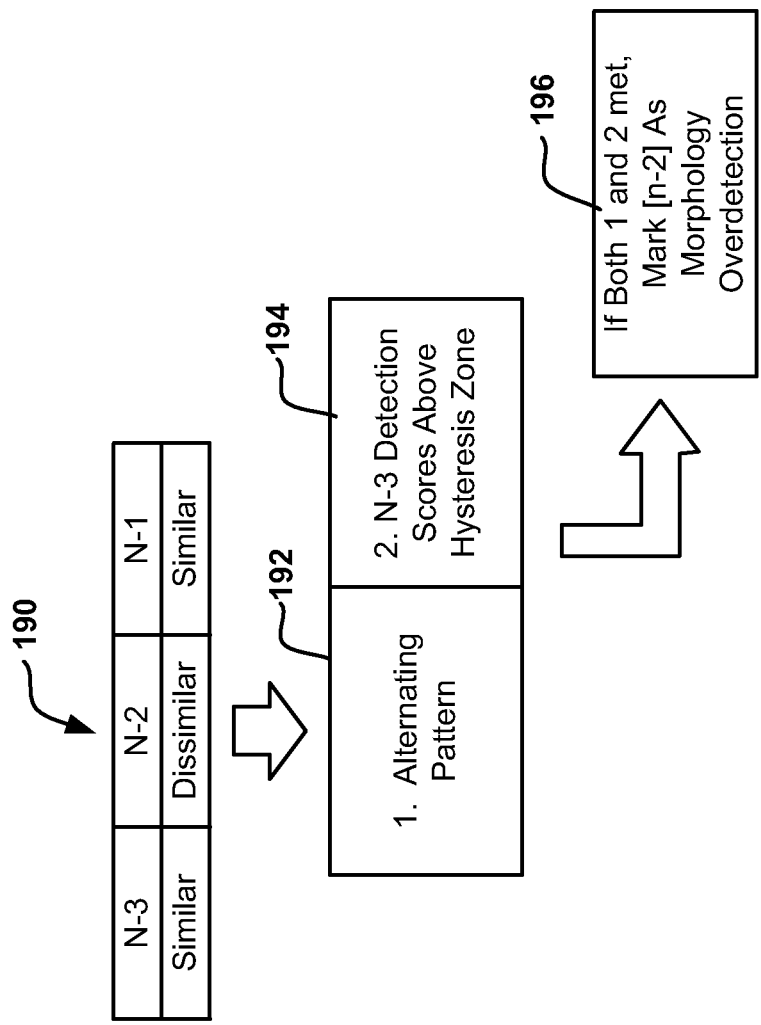
Figure 8:
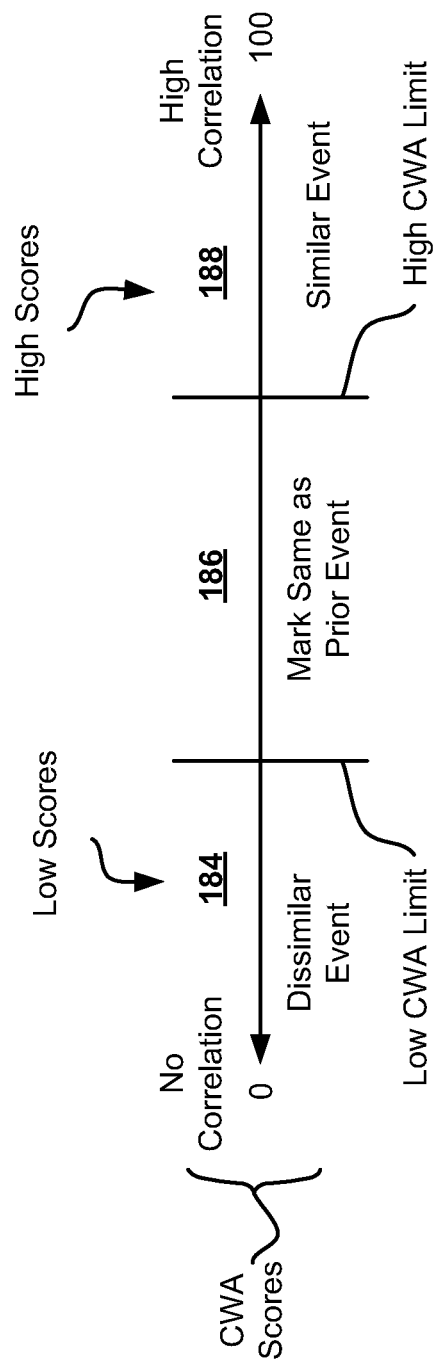
FIG. 8 shows an illustrative example of analysis to mark similar and dissimilar events in FIGS. 7A-7B.
Figure 9:
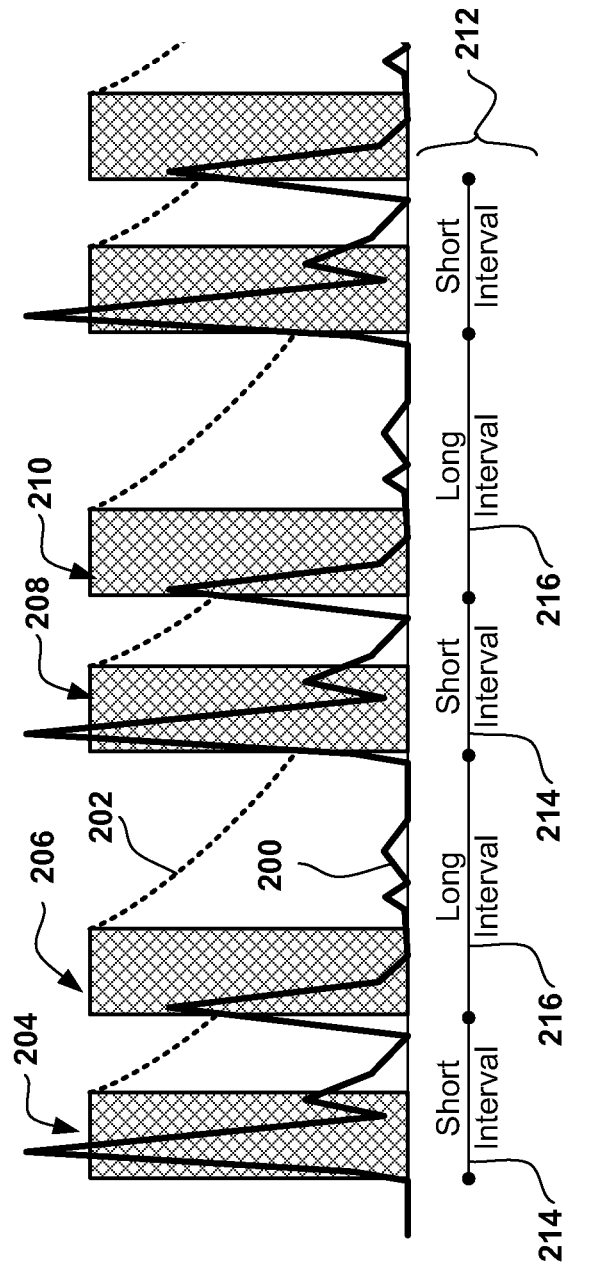
FIG. 9 shows an illustrative oversensed cardiac signal having alternating long-short-long intervals.
Figure 10:
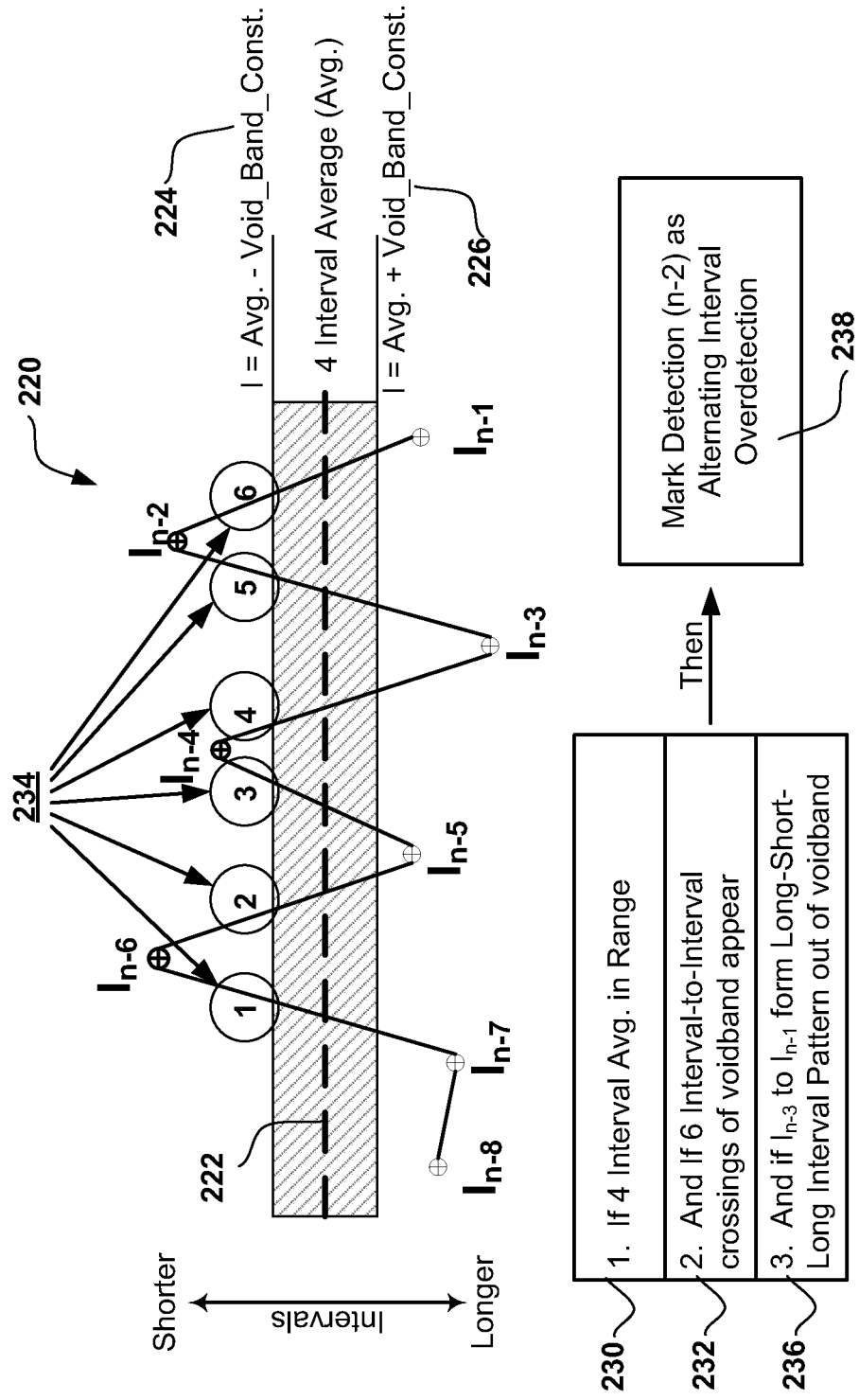
FIG. 10 illustrates analysis of an alternating interval overdetection identification method.

Next, the method performs an overdetection identification step 12. This may include one or more of several analysis methods including, as illustratively shown, morphology analysis 14, interval analysis 16 and wide QRS analysis 18. FIGS. 6A-6B, 7A-7B and 8 show illustrative morphology analysis 14 as part of overdetection identification 12. FIGS. 9-10 show illustrative interval analysis 16 as part of overdetection identification 12. FIGS. 11, 12A-12D, 13A-13B, and 14-15 show illustrative wide QRS analysis 18 as part of overdetection identification 12. FIG. 16 shows an example in which calculated beat rate is used to select from several overdetection identification methods 14, 16, 18.

Following overdetection identification 12, if one or more overdetections are identified, the method corrects data, as shown at 20. FIGS. 18-21 show illustrative data correction methods that can be performed in step 20. If no data correction is needed at step 20, the method may simply go to the next step.

Finally, the method includes a therapy decision, as shown at 22. A therapy decision 22 may classify a cardiac rhythm of the implantee. The therapy decision 22 may incorporate additional methods such as charge confirmation shown in FIG. 22. The method then iterates to event detection 10, as indicated by line 24.

The therapy decision 22 may include one or more of several forms of analysis. In one illustrative example, individual detected events are marked as shockable or non-shockable and an X-out-of-Y counter is maintained to determine whether the overall cardiac rhythm merits therapy. The marking of individual events as shockable or non-shockable may take several forms, including rate-based and/or morphology based determinations, or combinations thereof. Some illustrative factors and combinations of factors that may be considered are discussed in U.S. Pat. No. 6,754,528, entitled APPARATUS AND METHOD OF ARRHYTHMIA DETECTION IN A SUBCUTANEOUS IMPLANTABLE CARDIOVERTER/DEFIBRILLATOR, and U.S. Pat. No. 7,330,757 entitled METHOD FOR DISCRIMINATING BETWEEN VENTRICULAR AND SUPRAVENTRICULAR ARRHYTHMIAS.

Therapy decision 22 may also take into account the persistence of a malignant condition. Some illustrative examples are shown in U.S. Pat. Application Publication Number 2006/0167503, now issued as U.S. Pat. No. 8,160,697, titled METHOD FOR ADAPTING CHARGE INITIATION FOR AN IMPLANTABLE CARDIOVERTER-DEFIBRILLATOR. Other methods may be used as a part of the therapy decision 22. A detailed example using multiple rate zones for identifying shockable events in the therapy decision 22 is further discussed below.

The method of FIG. 1 includes overdetection identification 12 and data correction 20. These steps are designed to improve classification outcomes. The examples below provide details for implementing these steps in some illustrative embodiments.

Figure 2:
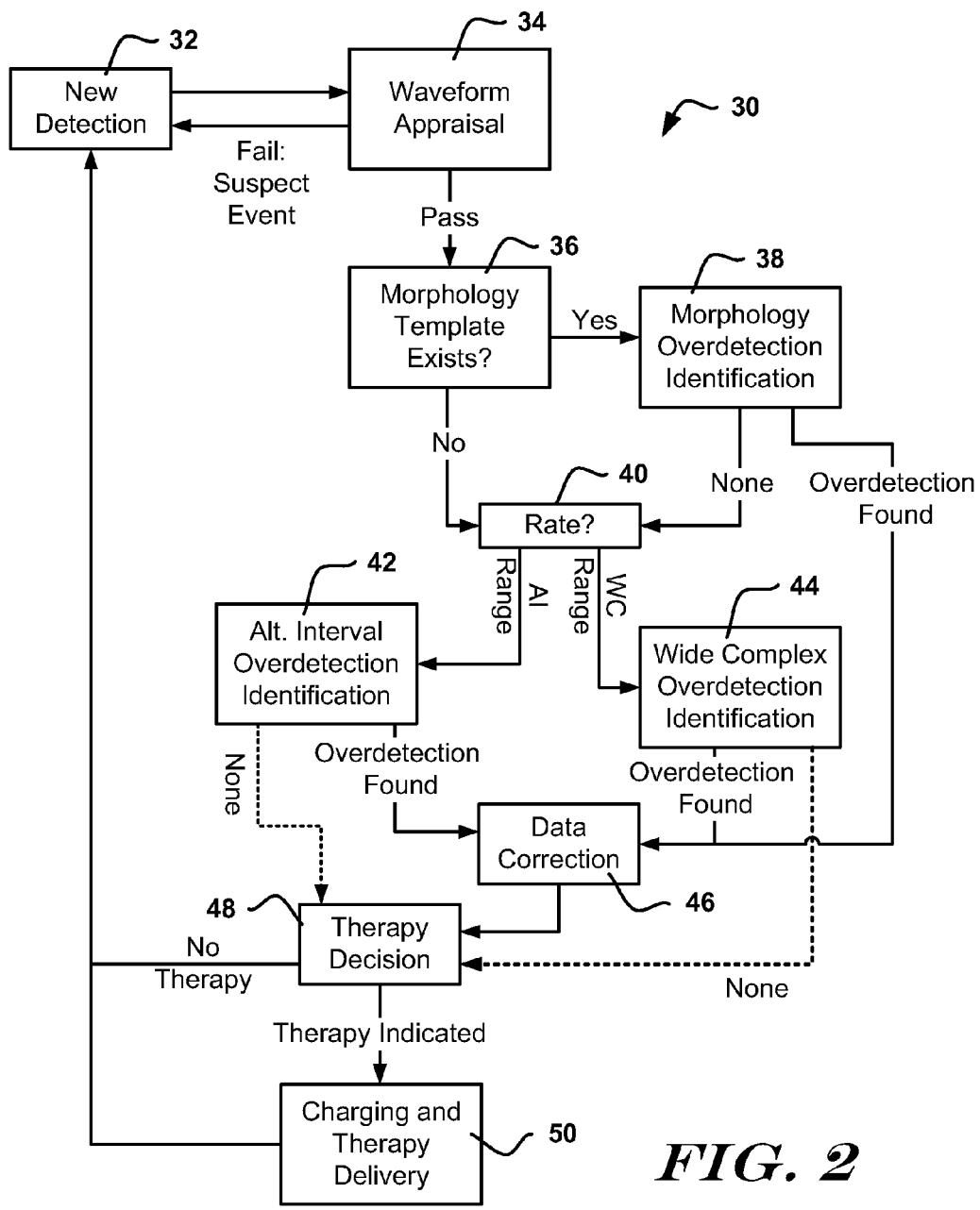
FIG. 2 is a block diagram further illustrating an example of identifying overdetection and making therapy decisions.

FIG. 2 is a process flow diagram further illustrating an example of identifying overdetection and making therapy decisions. The method 30 provides an example which incorporates each of several different overdetection identification steps, as well as additional analysis of captured data for waveform appraisal. The illustrative method begins with the declaration of a new detected event, as shown at 32 (again reference is made to FIGS. 4-5 and/or 17 to show detection threshold usage in step 32).

The detected event undergoes waveform appraisal as indicated at 34. Waveform appraisal 34 analyzes data captured in association with the detected event to ensure the detection is cardiac in origin. Waveform appraisal can mark detected events having significant noise as suspect events. For example, noise may be identified by counting the number of zero crossings of the signal, or of the first or second derivative of the signal, during a predetermined time period. U.S. Pat. No. 7,248,921, titled METHOD AND DEVICES FOR PERFORMING CARDIAC WAVEFORM APPRAISAL provides additional detailed examples of waveform appraisal 34.

If the detected event fails waveform appraisal 34, it is marked as a suspect event and the method returns to step 32 and awaits a next detection threshold crossing. Once a detected event is captured that passes waveform appraisal 34, the method 30 goes into steps for analyzing detections and identifying overdetection. As shown at 36, the illustrative method 30 determines whether a morphology template exists. A morphology template is a data set useful for morphological comparison with recently detected event(s). Morphology templates may be formed by implanted device systems or associated programmers, or may be selected or identified by medical personnel. U.S. Pat. No. 7,376,458, entitled METHOD FOR DEFINING SIGNAL TEMPLATES IN IMPLANTABLE CARDIAC DEVICES discusses some examples of template formation and/or testing. In some examples, template formation is performed by identifying a representative QRS complex that is reflective of an average or typical morphology of a cardiac cycle for an implantee.

In an illustrative example of automatic template formation, a detected event is identified and data for the detected event is stored by a device as a preliminary template. In the illustrative example, the preliminary template can be validated by comparing the stored data to data captured for a number of adjacent-in-time detected events. If the set of adjacent-in-time detected events demonstrates high correlation to one another, the preliminary template is validated and a morphology template is defined using the preliminary template. If the preliminary template cannot be validated, it is discarded. Template formation may fail if the captured signal persistently varies, since high variability may prevent validation of a preliminary template. The query at step 36 determines whether a template is available for use in morphology overdetection identification 38.

In some systems, a morphology template will always exist. For example, some embodiments allow a physician to select a representative beat during implantation or during a telemetry session as a morphology template, or a representative template may be selected from a library of known templates. If so, step 36 may be omitted.

At step 38, the morphology of one or more detected events is analyzed to determine whether one or more detected events is likely the result of overdetection. Steps as shown below with reference to FIGS. 6A-6B, 7A-7B and 8 may be performed as part of step 38. This may include identifying alternating patterns of morphology indicating High-Low-High correlations to the morphology template.

Following step 38 (if a stored morphology template exists) or step 36 (if there is no stored morphology template), the method continues at 40, where the measured heart rate of the implantee is considered. If the rate falls into an AI Range (short for Alternating Interval Range) the illustrative example proceeds with Alternating Interval Overdetection Identification as shown at 42. In Alternating Interval Overdetection Identification 42, the intervals between detected events are analyzed to determine whether overdetection is occurring. The Alternating Interval Overdetection Identification 42 method may include steps as shown below with reference to FIGS. 9-10.

Returning to step 40, if the implantee heart rate falls into the WC Range (Wide QRS Complex range), then Wide Complex Overdetection Identification methods are called, as indicated at 44. Wide Complex Overdetection Identification 44 is designed to identify overdetection of wide QRS complexes, and may include the methods discussed below with reference to FIGS. 11, 12A-12D, 13A-13B and 14-15.

The AI Range and WC Range may be separate from one another, or there may be overlap of these ranges such that each of steps 42 and 44 are performed. Further discussion of the integration of these methods is set out with reference to FIG. 16, below. In yet another embodiment, each of steps 42, 44 are performed regardless of the calculated heart rate.

In FIG. 2, following the applicable overdetection identification steps 38, 42 and/or 44, data correction may be invoked, as shown at 46. Data correction 46 is invoked when one or more of the overdetection identification steps 38, 42 and/or 44 identifies overdetection. If no overdetection is identified, data correction 46 may be bypassed.

In some examples, data correction includes recalculation of intervals between detected events by removing one or more identified overdetections from analysis. For example, if an overdetection is identified, then step 46 can manipulate stored data to correct for the overdetection and reduce the calculated heart rate. FIGS. 18-21 further illustrate this concept in a particular series of examples.

The examples of FIGS. 18-21 buffer rate calculations from ongoing detections by waiting until an interval between two detections is "certified" before using the interval for rate calculation. In some examples, an interval is considered certified if it passes waveform appraisal 34 and the several overdetection identification steps 38, 42, 44 without being marked as noise or as an overdetected event.

Following data correction 46, the method makes a therapy decision 48. If no therapy is needed, the method returns to block 32. If therapy is indicated at step 48, then charging and therapy delivery steps can be performed, as shown at 50. Typically, implanted therapy devices use charging circuitry that takes a period of time to prepare the device for therapy delivery. The method may iterate several times after a charge is initiated before therapy can be delivered. The specifics of steps 48 and 50 may vary. Once therapy is indicated at 48, a system may ensure that therapy continues to be indicated until it is delivered. U.S. Patent Application Publication Number 2006/0167503, now issued as U.S. Pat. No. 8,160,697, titled METHOD FOR ADAPTING CHARGE INITIATION FOR AN IMPLANTABLE CARDIOVERTER-DEFIBRILLATOR provides some illustrative examples of these concepts.

Figure 3:
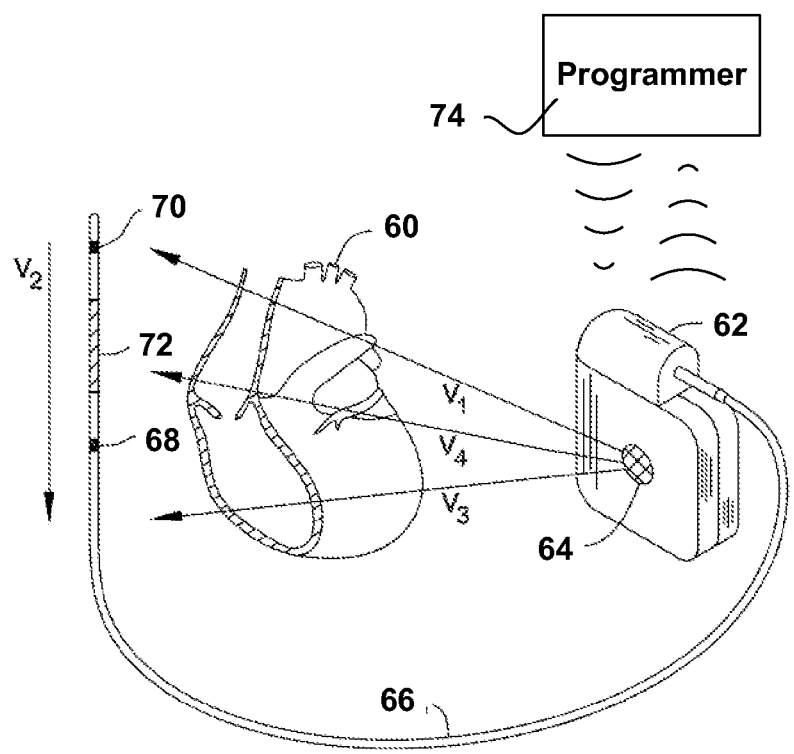
FIG. 3 shows an illustrative implantable medical device.

FIG. 3 shows an illustrative implantable medical device and implant location. More particularly, an illustrative subcutaneous-only system is shown in FIG. 3. The subcutaneous system is shown relative to a heart 60, and includes a canister 62 coupled to a lead 66. The canister 62 preferably houses operational circuitry for performing analysis of cardiac activity and for providing a therapy output. The operational circuitry may include batteries, input/output circuitry, power capacitors, a controller, memory, telemetry components, etc., as known in the art.

Electrodes are disposed at locations throughout the system including, for example, an electrode 64 on the canister 62, and electrodes 68, 70, 72 on lead 66. The electrodes 64, 68, 70, 72 may take any suitable form and can be made of any suitable material. For example, the canister electrode 64 may be an isolated button electrode or it may be a region or surface of the canister 62, and the electrodes 68, 70, 72 on lead 66 may be coil electrodes, ring electrodes, or other structures known in the art.

The electrodes 64, 68, 70, 72 define a plurality of sensing vectors such as V1, V2, V3 and, optionally, V4. If desired, one or more vectors V1, V2, V3, and V4 may be chosen as a default sensing vector, for example, as discussed in U.S. Patent Application Publication Number 2007-0276445 titled SYSTEMS AND METHODS FOR SENSING VECTOR SELECTION IN AN IMPLANTABLE MEDICAL DEVICE. Other uses of multiple vectors are shown, for example, in U.S. Pat. No. 7,392,085 titled MULTIPLE ELECTRODE VECTORS FOR IMPLANTABLE CARDIAC TREATMENT DEVICES. Another embodiment considers posture in vector analysis, for example, as discussed in U.S. Patent Application Publication Number 2008-0188901, now issued as U.S. Pat. No. 8,200,341, titled SENSING VECTOR SELECTION IN A CARDIAC STIMULUS DEVICE WITH POSTURAL ASSESSMENT. Multiple sensing vectors may be analyzed, sequentially or in combination, as desired.

The present invention is not limited to any particular hardware, implant location or configuration. Instead, it is intended as an improvement upon any implantable cardiac system. Some illustrative examples can associate with an external programmer 74 configured to communicate with the implanted device for various purposes, including, for example and without limitation, one or more of the following: device testing; upload new/revised software; modify sensing, detection or therapy settings; determine the status of device operation, battery life, or lead integrity; and/or download data relating to the implantee's condition, prior data capture, or treatment. Any suitable communication method may be used, such as various protocols and hardware widely known in the art.

FIG. 3 omits several anatomical landmarks. The illustrative system shown may be implanted beneath the skin outside of the ribcage of the implantee. The location illustratively shown would place the canister 62 at approximately the left axilla of the implantee, level with the cardiac apex, with the lead 66 extending medially toward the xiphoid and then toward the head of the implantee along the left side of the sternum. One illustrative example uses a method/system as shown in commonly assigned U.S. Patent Application Publication Number 2006-0122676 entitled APPARATUS AND METHOD FOR SUBCUTANEOUS ELECTRODE INSERTION, now U.S. Pat. No. 7,655,014. Other illustrative subcutaneous systems and locations are shown in commonly assigned U.S. Pat. Nos. 6,647,292, 6,721,597 and 7,149,575.

The present invention may also be embodied in systems having various implant configurations including, for example, other subcutaneous-only, vascular-only, and/or transvenous implantation configurations/locations. The canister 62 may be placed in anterior, lateral, and/or posterior positions including, without limitation, axillary, pectoral, and sub-pectoral positions, as well as placements on either the left or right side of the implantee's torso and/or in the abdomen. Entirely intravascular implantation of the system has also been proposed. The lead 66 may be placed in any of a number of suitable configurations including anterior-posterior combinations, anterior-only combinations, transvenous placement, or other vascular placements.

FIGS. 4-5 illustrate a detection profile and how its use, in given circumstances, may lead to overdetection. Referring to FIG. 4, a detection profile is shown at 80 as including a refractory period which is followed by an exponential decay. For illustrative purposes, the height of the refractory period is shown as the "Estimated Peak." The Estimated Peak is an implantable systems' estimate of the peak amplitude of captured cardiac signals. The use of Estimated Peak allows the detection profile to adapt to the amplitude of captured signals.

The decay slope of detection profile 80 uses the Estimated Peak (or, in some embodiments, a percentage of the Estimated Peak) as its starting point. The decay approaches the sensing floor over time. The sensing floor may be the ultimate floor or highest sensitivity of the system, or it may be set to a predetermined level. Multiple decays may be used, as shown in U.S. Provisional Patent Application No. 61/034,938. The decay may be exponential or may take some other shape such as a straight-line decay, stepped function, etc.

FIG. 5 shows application of the detection profile 80 from FIG. 4 to a captured signal, which is shown at 104. Refractory periods are shown in cross-hatching at 100, 106, 112, and 118. Exponential decays 102, 108, 114 follow each refractory period 100, 106, 112, 118. Where the detection profile meets the captured signal 104, a detected event is declared and a refractory period starts. Thus, when exponential decay 102 meets the captured signal 104, a detected event is declared and a refractory period 106 starts. In the example shown, overdetection occurs when the T-waves are detected, as occurs in association with refractory periods 106, 118 in addition to the R-waves associated with refractory periods 100, 112.

In the illustrative example of FIG. 5, the Estimated Peak is calculated as the average of two previous peaks. As can be seen at 120, the Estimated Peak (represented as the height of the refractory periods 100, 106, 112, 118) drops following the overdetection associated with refractory period 106, as the newly calculated Estimated peak is an average of R-wave and T-wave amplitudes. This may increase the likelihood of further overdetection by lowering the Estimated Peak to a level that is closer to more signal peaks that represent potential sources of overdetection.

Morphology Overdetection Identification

Some embodiments of the present invention provide example methods to identify and correct overdetection. FIGS. 6A-6B, 7A-7B, and 8 present morphology-based approaches to identifying overdetection using correlation. For illustrative purposes, these methods are applied to the overdetection shown in FIG. 5.

Some illustrative embodiments of morphology overdetection identification identify alternating morphology patterns. For example, during overdetection, some events may correlate highly to a stored template while other events may correlate poorly (indicating overdetections), in an alternating pattern. When a sequence of comparisons yields High-Low-High correlations, the pattern may be attributed to overdetection. As shown below, the Low correlated detected events can then be marked as overdetections. An alternating sequence is one type of pattern, but other patterns may be sought instead. In another example, triple detection may be identified by the use of High-Low-Low triplets, and in yet another example, rather than a stored, static morphology template, a series of detections may be compared one to another, making each new detection a separate template. Yet another example uses a dynamic template that changes over time, for example, by integrating new detections into the template, or by averaging a plurality of previously detected events.

Referring now to FIG. 6A, correlation waveform analysis is shown. A portion of signal within the refractory period 100 in FIG. 5 is shown at 130 in defined sample window 132. FIGS. 6A-6B show the unrectified signal, while FIG. 5 shows the rectified signal. The sample window 132 defines a number of samples 134, which are shown as a continuous line for simplicity, as an understanding of "sampling" an analog signal into the digital domain is considered to be within the knowledge of those skilled in the art.

The sample window also defines the alignment of the samples 134 around a fiducial point (typically the maximum amplitude point) in the captured signal. Some illustrative methods for defining a sample window are discussed in U.S. Pat. No. 7,477,935 entitled METHOD AND APPARATUS FOR BEAT ALIGNMENT AND COMPARISON.

While some embodiments may use the refractory period to define the sample window 132, other embodiments tailor the sample window 132 using features of the template 136. In an illustrative embodiment, the template 136 can be formed by analyzing one or more detected events to identify QRS begin and end points, as well as their position relative to a fiducial point (such as the peak during refractory). These features can be used to define the stored template so it approximates the QRS complex. Other template types may be used, including, for example, data transforms and set reduction techniques. Some templates may also rely on multi-channel sensing.

The samples within the sample window 132 are compared to the stored template, which is graphically shown at 136. The specific mathematical analysis of a template comparison may vary. Morphology analysis may include, for example and without limitation, Correlation Waveform Analysis (CWA), reduced data set analysis including peak-feature-location identification and comparison, wavelet transformation, Fourier transformation, signal decomposition such as source separation, or other data analysis methods such as compression methods. For simplicity, in the following examples, reference is made to comparison in the form of correlation/CWA, with the understanding that these other analysis methods may be substituted in other illustrative embodiments. CWA may take use a simplified calculation of the sum of absolute values of differences between a template and a signal under analysis, or CWA may use an approach in which the squares of differences between signal samples and template samples are calculated and used to find correlation. Simplified methods may be used to reduce computational expense.

With respect to the comparison in FIG. 6A, it can be noted that, as stated above, the signal at 130 comes from the refractory period at 100 in FIG. 5, which corresponds to the R-wave of a cardiac cycle. As a result, there is good correlation of the captured R-Wave to the morphology template.

FIG. 6B shows the signal 140 derived from samples adjacent the peak in the refractory period 106 (FIG. 5) that occurs in association with overdetection of a T-wave. As may be expected, the signal 140, as windowed at 142, displays poor correlation to the stored template 136. Thus, the accurate detection in FIG. 6A shows good correlation to the stored template, while the overdetection in FIG. 6B displays poor correlation to the stored template. FIGS. 7A-7B and 8 illustrate how these features of the overdetection in FIG. 5 may be used to identify overdetection.

Referring to FIG. 7A, a series of detections and associated refractory periods are displayed at 148, with the signal rectified. Unrectified signal is shown at 150 including detected events 152, 154, 156. For illustration, the events are numbered as shown at 148: event 156 is the N-1 event, event 154 is the N-2 event, and event 152 is the N-3 event. The event that is the most recent is shown at the far right of the event detection graphic 148. The detections 150 correspond to an R-wave 152, a trailing T-wave at 154, and another R-wave at 156. Sample windows 160, 162, 164 are defined for each detection 152, 154, 156. In the example, the fiducial point of each sample window is shown as a vertical line. The fiducial point is offset to the left of the sample windows 160, 162, 164; an offset fiducial point may be used but need not be the case.

Next, the signal samples within each sample window 160, 162, 164 are compared to a template 172, as shown at 170. The comparison outcomes are shown as percentage correlations, indicated at 174. As shown, the score for R-wave 152 is high (95%), indicating strong correlation to the template 170. This makes R-wave 152 "Similar" to the template, as indicated. Likewise, the score for R-wave 156 is high (90%), again indicating strong correlation to the template 170, thus, the "Similar" marking. However, the overdetected T-wave 154 does not correlate well to the template 170, and has a low correlation score (5%) and is marked "Dissimilar". The numbers provided in FIG. 7A at 174 are provided only for illustration and are not the result of actual computations.

Following calculation of scores at 174, the method next characterizes each score, as indicated at 182. An illustrative characterization method is shown in FIG. 8. Referring to FIG. 8, CWA is referenced, with scores provided on a scale from 0-100%. Three zones of comparison are shown at 184, 186, and 188. Scores falling within the first zone 184 are considered dissimilar from the stored template, while scores falling within the third zone 188 are considered similar to the stored template. The second zone 186 is treated as a hysteresis band in which events are marked the same as the prior event, for example, an event falling within the second zone 186 that follows an event falling in the third zone 188 would be marked "similar". In an illustrative example, the boundary between the first and second zones 184, 186 is set to about 25% correlation, while the boundary between the second and third zones is set to about 52% correlation. Other boundaries and/or forms of this analysis to mark similar and dissimilar events relative to a template may be used.

Referring back to FIG. 7A, the comparison scores 174 are characterized as shown at 182. The second detection 154 is a T-wave and, due to a low comparison score, is marked "Dissimilar", while the other two detections are marked as "Similar." The "Similar" and "Dissimilar" markings are used for applying a comparison overdetection rule which is shown in FIG. 7B. The rules rely in part on the pattern shown at 190, in which the events N-1, N-2, N-3 form a similar-dissimilar-similar pattern. There are two parts to the comparison overdetection rule:

A) As shown at 192, an alternating pattern 190 is sought; and
B) As shown at 194, the N-3 detection must score "High" and above the Hysteresis zone 186 in FIG. 8.

As can be appreciated from the manner in which events are marked, rule 194 effectively ensures that none of the three detections (N-1, N-2, N-3) has a correlation score that falls into the hysteresis zone 186.

As indicated at 196, if both rules are met, then the method marks one of the events (N-2) as a Morphology Overdetection. In the illustrative example, the analysis contemplates events N-3, N-2 and N-1. The timing of analysis (using events N-1, N-2 and N-3 but not event N) is merely illustrative, and the present invention is not limited to any particular architecture with respect to the timing of analysis of individual events.

The use of the overdetection marker is further discussed below with reference to FIGS. 18-21. Generally speaking, the method in FIGS. 18-21 does not differentiate Morphology Overdetection from other detections, however, if desired, the treatment of overdetection(s) may vary depending upon the identifying method. In another embodiment, data relating to which type of Overdetection Analysis has identified overdetection(s) may be retained to help analyze device operation, for example, to allow refinement of the detection profile and/or the Overdetection Analysis.

In addition to the morphology analysis, interval timing may be considered. In one embodiment, the Morphology Analysis Overdetection is omitted if the intervals between the three detections are greater than a threshold, such as 500-1000 miliseconds. For example, it may be found that detections more than 800 milliseconds apart are unlikely to result from overdetection, or that an implantable system is unlikely to make any incorrect therapy decisions based on overdetection resulting in 800 millisecond intervals (equal to 75 beats-per-minute).

Alternating Interval Overdetection Identification

As indicated by FIGS. 1-2, another illustrative method for identifying overdetections uses event intervals to identify alternating interval patterns. It is believed that overdetection may be identified by analyzing the intervals between detected events. If analysis of a set of detected events indicates an alternating pattern of long-short intervals between events, overdetection may be occurring.

FIG. 9 provides an illustration of an alternating long-short-long interval pattern. In particular, a captured signal is shown at 200. A detection profile similar to that of FIG. 4 is applied to the captured signal 200. The result is consistent overdetection, with an R-wave detection shown in association with a refractory period at 204, and a T-wave detection shown in association with a refractory period at 206. This pattern repeats with detections associated with refractory periods at 208 and 210.

The intervals from detection to detection are shown and characterized at 212, including short intervals 214 and long intervals 216. In a numeric example, if the refractory periods are about 100 ms, then the short intervals may be in the range of 200 ms, while the long intervals are in the range of about 450 ms. This would result in a detected heart rate of about 184 beats-per-minute (bpm) with an actual cardiac rate of only 92 bpm, with the difference being attributed to persistent overdetection. A different duration for the refractory period may be used.

The long-short-long pattern provides another basis for identifying overdetection. The pattern may become more difficult to discern at higher rates, since the difference between long intervals 216 and short intervals 214 becomes less apparent. If desired, and as shown in FIG. 16, the alternating interval pattern analysis may be omitted when detected heart rates become relatively high.

FIG. 10 illustrates an alternating interval pattern. At 220, a mapping of interval durations is shown, with a center line shown at 222 as the average interval. Any suitable number of intervals may be used to calculate the average. A voidband having high and low boundaries is shown, with the short interval boundary shown at 224 and a long interval boundary shown at 226. The voidband is defined by a voidband constant in the example shown. Thus, for example, if the four interval average at a given point in time is 400 milliseconds (150 bpm), and a voidband constant of about 23 milliseconds is used (other voidband constants may be used), then the boundaries 224, 226 would be 377 milliseconds and 423 milliseconds, (142 to 159 beats bpm) respectively. A different voidband definition may be used instead, for example, simply +/−10 bpm, or an offset such as +10 milliseconds, −20 milliseconds.

In the illustrative example, in order to identify an alternating interval pattern, several rules are applied. First, the four interval average 222 must fall within a predetermined range, as indicated at 230. Some embodiments omit rule 230. Second, a specific pattern must be found, as indicated at 232. In the illustrative example, pairs of consecutive intervals are considered, and there must be at least six crossings of the voidband by a line drawn between each interval within the previous 8 intervals. Crossings of the voidband in the illustrative example of FIG. 10 are shown and numbered at 234. For example, interval $I_{n-5}$ is longer than the boundary 226, and interval In-4 is shorter than the duration defined by boundary 224. Thus, the pair $I_{n-5}$, $I_{n-4}$ crosses the voidband, increasing the count of interval pairs that satisfy the specific pattern 232. Other parameters may be used to identify the alternating intervals, if desired.

Another rule is shown at 236 and calls for a Long-Short-Long pattern in the three most recent intervals. Referring to FIG. 9, it can be seen that, when a Long-Short-Long pattern forms due to overdetection of T-waves, the Short interval likely corresponds to the time from the R-wave detection to the T-wave detection. The rule 236 calls for identifying a set of Long-Short-Long intervals in the intervals for N-1 to N-3.

As shown in FIG. 10 at 238, if each rule 230, 232, 236 is met, then detection N-2 is marked as an alternating interval overdetection. The incorporation of overdetection marking into a rate calculation method is further illustrated by FIGS. 18-21, below. FIGS. 18-21 illustrate selective correction of data for rate calculation; however, such data correction could interfere with the Alternating Interval Overdetection Identification method by combining intervals, removing the short intervals and preventing the noted voidband crossings. Within the alternating interval analysis, the identification of an overdetection does not change the handling of detected events. Therefore, in an illustrative example, Alternating Interval Overdetection Identification methods make use of raw, uncorrected intervals (based on detections that pass waveform appraisal) to establish the Average Interval and to identify excursions below and above the voidband, rather than using corrected intervals.

Analysis as shown in FIG. 10 is one example of an Alternating Interval analysis. Other Alternating Interval analysis may look for other time or interval based patterns in a queue of intervals between detected events. Examples include triple detection (long-short-short triplets), combinations (sets where three intervals are captured, with the second and third interval being approximately as long as the first interval, indicating a correct detection followed by a double detection pair), or any other suitable timing-based pattern analysis.

Wide Complex Overdetection Identification

Some embodiments of the present invention are directed toward identifying overdetection of wide QRS complexes. FIGS. 11, 12A-12D, 13A-13B, and 14 illustrate Wide Complex Overdetection Identification. The Wide Complex Overdetection Identification methods observe whether detections occur within short intervals and with predetermined morphology characteristics. If the proximity and morphology characteristics are identified, the Wide Complex Overdetection Identification method determines that overdetection has occurred.

Figure 11:
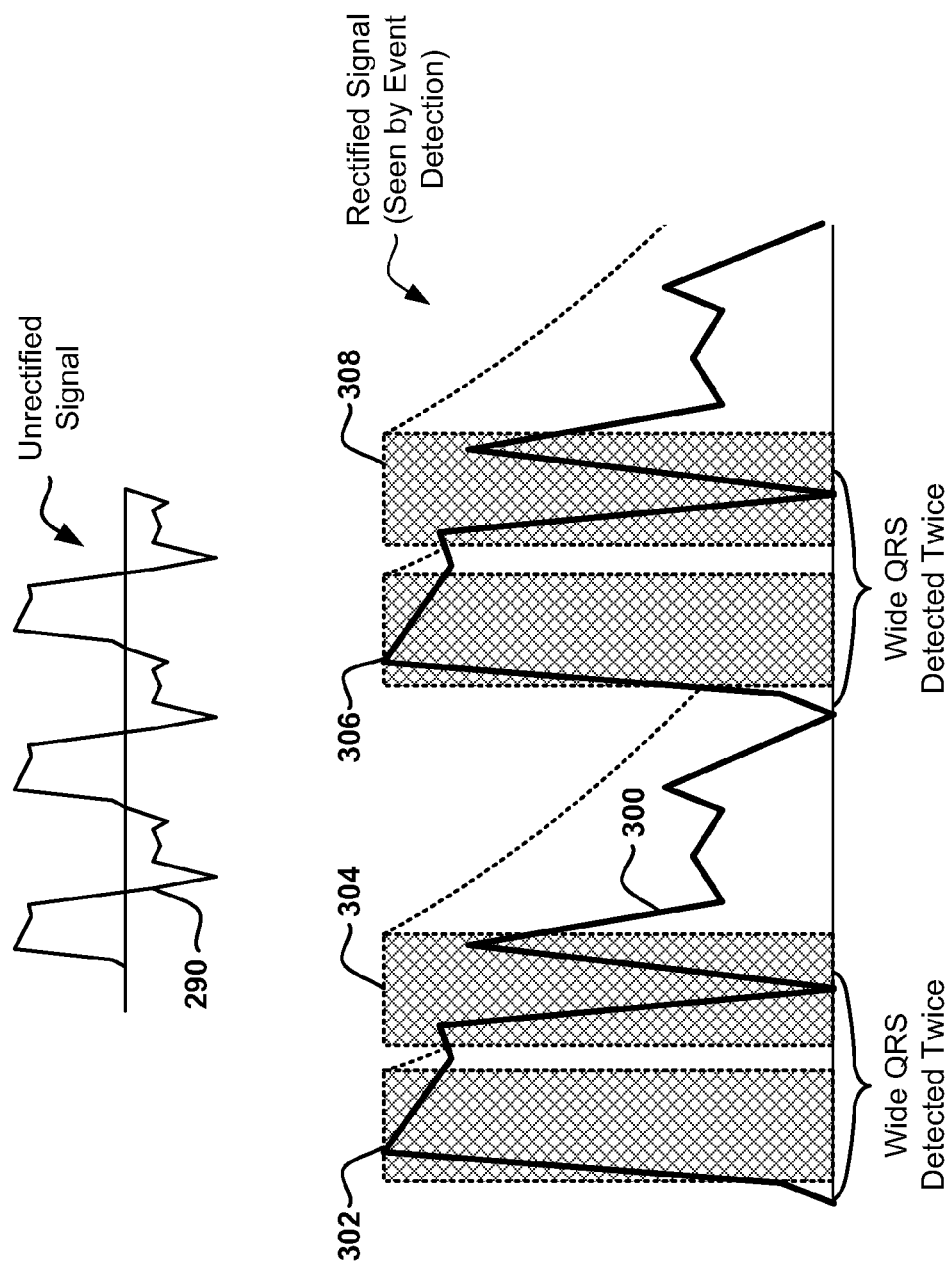
FIG. 11 shows an illustrative oversensed wide QRS complex.

Referring now to FIG. 11, the unrectified signal is shown as signal 290. The signal 290 demonstrates a wide QRS complex. The rectified version of the signal 290 is shown at 300. As can be seen at 302, 304, the wide QRS is detected twice. This pattern repeats itself again at 306, 308.

Figure 12A:
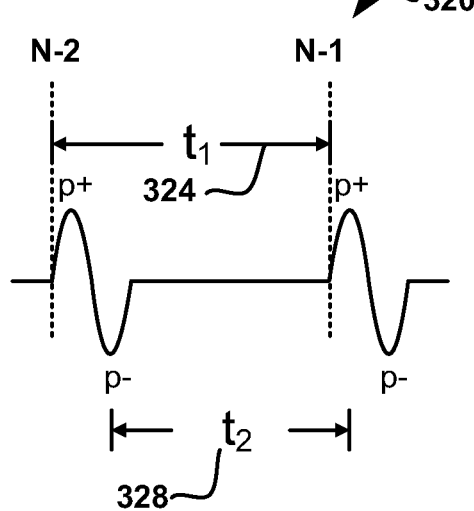
FIGS. 12A-12D show illustrative application of wide-complex overdetection identification rules.
Figure 12B:
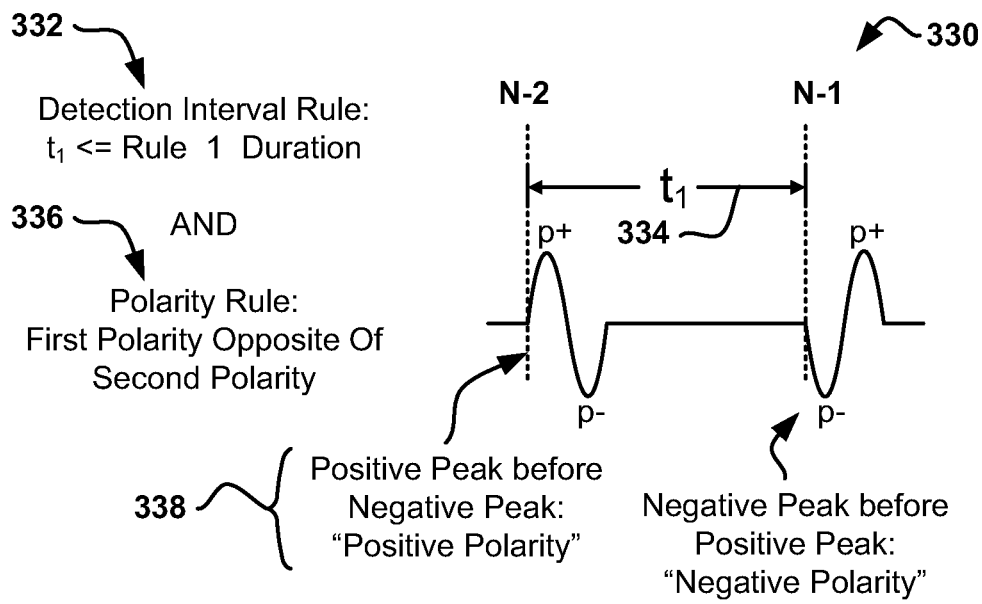

FIGS. 12A and 12B show two rule combinations that can be used, either alone or as alternatives to one another, for identifying wide complex double detections. In FIG. 12A, at 320, detections N-1 and N-2 are shown. For purposes of applying the rule set, positive and negative peaks of each detection are marked as "p+" and "p−", respectively. The positive peak, p+, is marked at the point of maximum (or most positive) signal amplitude, and the negative peak, p−, is marked at the point of minimum (or most negative) signal amplitude during each refractory period.

FIG. 12A shows a first wide complex rule set. A first rule is shown at 322 and is labeled the Detection Interval Rule. The first rule 322 calls for the interval between the detections (shown as $t_1$ 324) to be less than a predetermined value, noted as Rule__1_Duration. The second rule 326 is labeled the Peak Proximity Rule and calls for a time $t_2$ 328 that is the duration between the latter peak (here, p−) of the N-2 detection and the earlier peak (here, p+) of the N-1 detection to be less than another predetermined value, noted as Rule__2_Duration (it should be noted that time is not shown to scale).

In an illustrative example, Rule__1_Duration is set to about 195 milliseconds. In another illustrative example, Rule__1_Duration is set to the sum of the duration of the refractory period plus about 40 milliseconds. In an illustrative example, Rule__2_Duration is set to about 20 milliseconds. Other values may be used for Rule__1_Duration and Rule__2_Duration. Some examples set Rule__1_Duration within a range of 150-240 milliseconds, or, in other examples, the refractory duration plus 20-60 milliseconds. Some examples set the Rule__2_Duration in the range of 10-40 milliseconds. Other formulations may be used as well.

FIG. 12B shows a second wide complex rule set. In FIG. 12B, at 330, a set of detections N-1 and N-2 are shown, with positive and negative peaks marked with p+ and p− indicators. A first rule is shown at 332 as a Detection Interval Rule in which the interval t1 334 between the detections is compared to Rule__1_Duration. The second rule is shown at 336 and is referred to as a Polarity Rule. The Polarity Rule determines whether the N-1 and N-2 detections are of opposing "polarity." For the purposes of the Polarity Rule, a detection is considered as having positive polarity if the p+ peak occurs before the p− peak; otherwise, the detection is negative. If the polarities of the two detections N-1 and N-2 are not the same, as shown, then the second rule 336 is met.

Figure 12C:
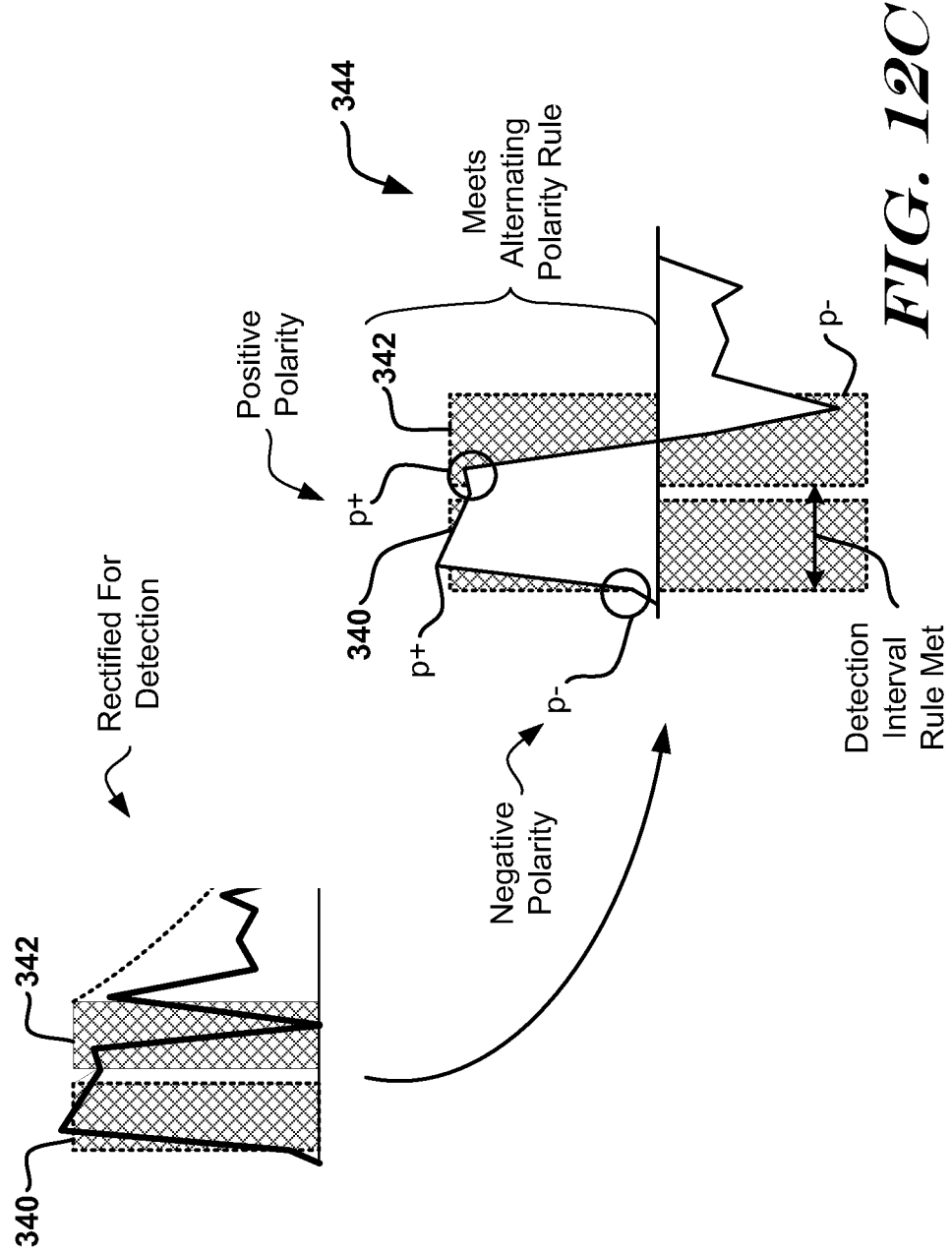
Figure 12D:
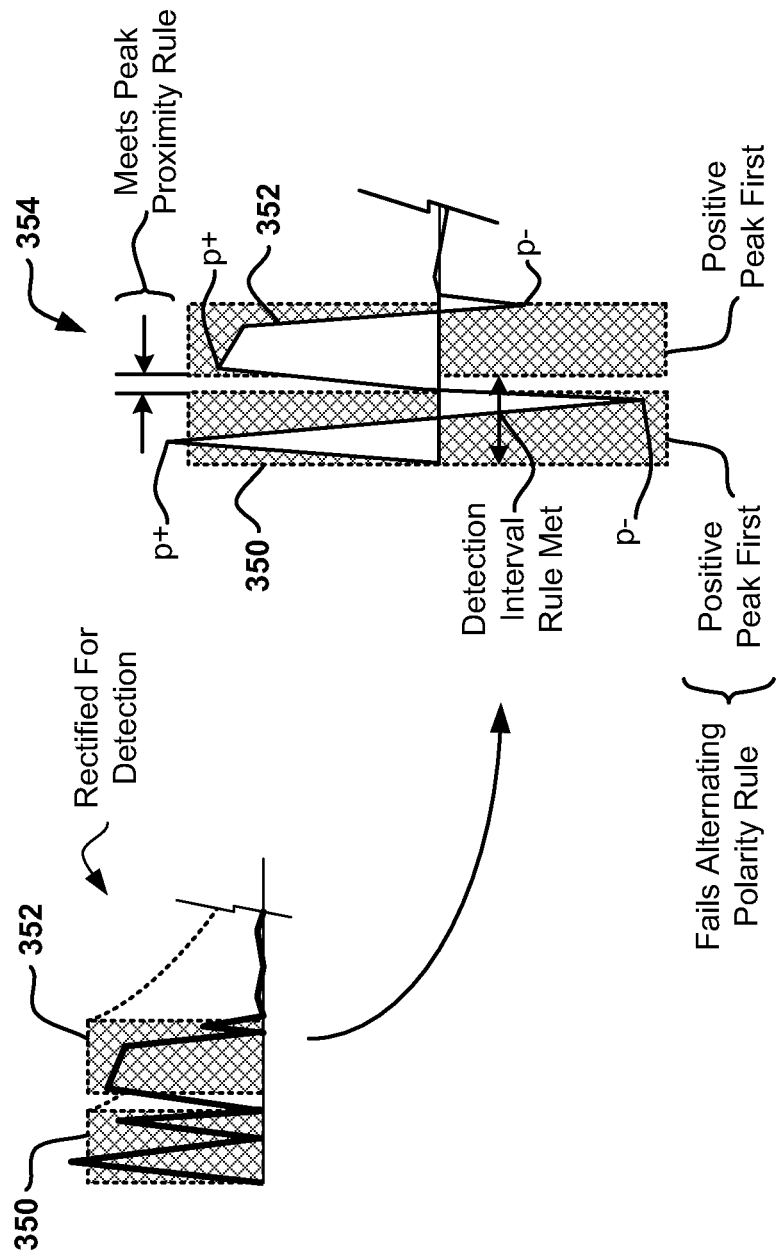

The signals shown in FIGS. 12A-12B are simplified to highlight the use of p+ and p− markers for identifying peak proximity and polarity. FIGS. 12C and 12D provide examples simulating more realistic signals in which wide QRS complexes are overdetected.

FIG. 12C illustrates application of a Wide Complex rule set to an overdetected signal having a wide QRS complex. The rectified version of the signal is shown in the upper portion of FIG. 12C to illustrate detections 340 and 342 occurring as the wide complex is overdetected. The unrectified signal is shown at 344. For a one-sided signal as shown, the negative peak p− can be defined as the lowest amplitude sample. The first detection 340 has p− occurring before p+. By definition, this gives the first detection 340 negative polarity.

For the second detection, the p+ occurs first, giving the second detection positive polarity. Because the first detection has negative polarity and the second detection has positive polarity, the polarity rule is met. As noted, the detection interval rule is met. As a result, both the first and second rules noted in FIG. 12B are satisfied by the detected event pattern shown in FIG. 12C.

FIG. 12D illustrates application of another Wide Complex rule set to another signal. Again two detections 350, 352 are shown in rectified form for detection purposes. In FIG. 12D, the alternating polarity rule fails because the first event 350 and second event 352 both have positive polarity, with the positive peak of each occurring first. Meanwhile, the detection interval rule is met. In the example, the peak proximity rule is met because p− for the first detection 350 is near the end of the refractory period, while p+ for the second detection 352 is near the start of the refractory period.

Rule sets are met in each of FIGS. 12C-12D. FIG. 13A shows how satisfaction of a rule set may be handled. FIG. 13B shows how events can be marked for purposes of rate calculation in FIGS. 18-21 using the rule set results and other conditions.

Figure 22:
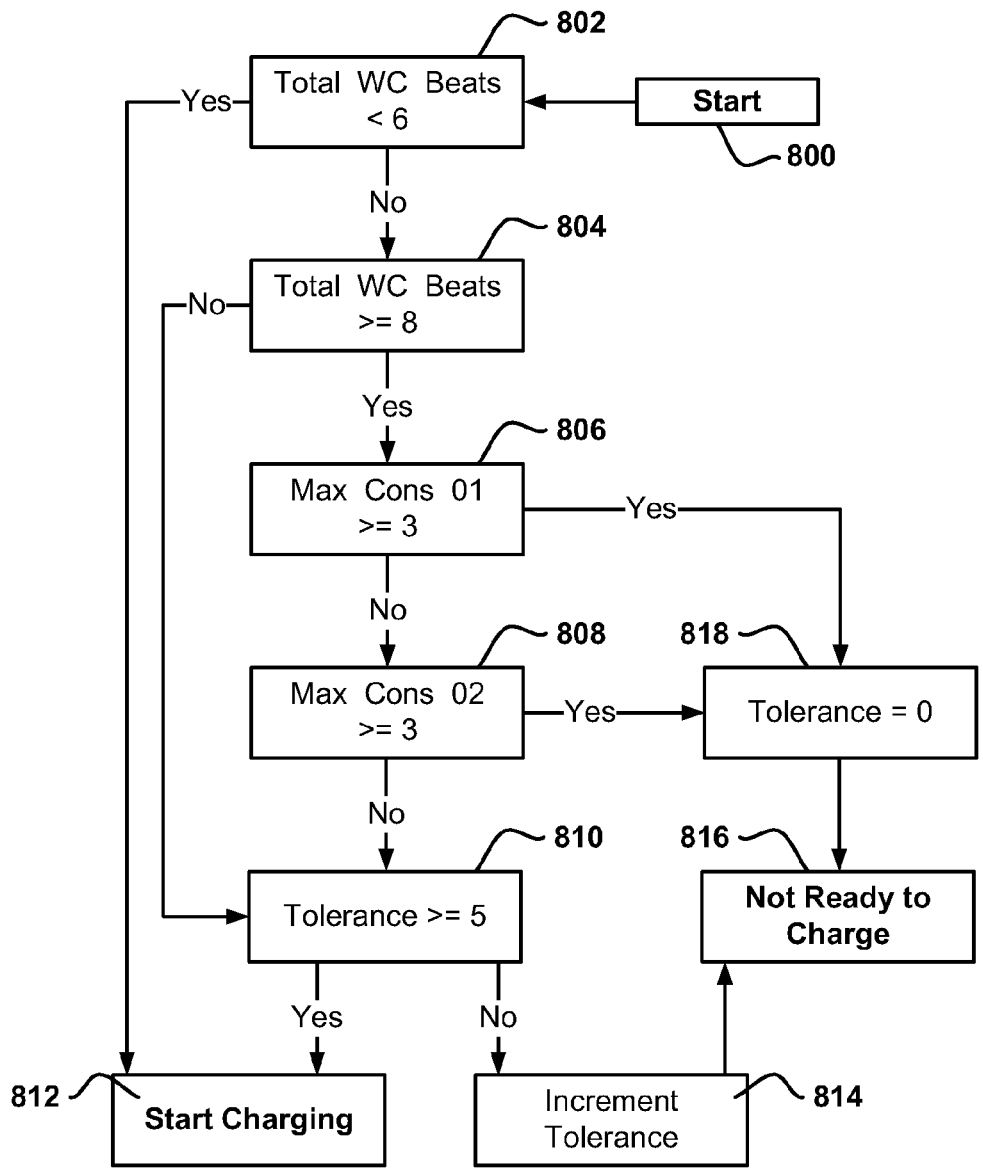
FIG. 22 is a process flow diagram for an illustrative charge confirmation method.

As shown in FIG. 13A, the Wide Complex Overdetection Identification method uses "True" and "False" markers for individual detected events. These markers indicate the confidence the system has in the individual detections. A "False" marking indicates a lack of confidence in a given detection, meaning that the analysis of the Wide Complex Overdetection Identification method has found that the False detection is likely an overdetection. A "True" marking indicates that the wide complex analysis has not identified a given detection as a likely overdetection. If large numbers of detections are marked False, overdetection is suspected. FIG. 22 provides an example of a charge confirmation method that may be used to verify therapy decisions before preparations for therapy delivery are made if large numbers of detections are marked False.

The True-False marking of FIG. 13A may be performed regardless of heart rate. In an illustrative example, the additional marking shown in FIG. 13B of individual events as Wide Complex Overdetections and/or Wide Complex Suspect is performed only while the detected rate is in a predetermined range (FIG. 16). This heart rate range limit on Wide Complex Overdetection marking and/or Wide Complex Suspect marking may be omitted in some embodiments.

Referring to FIG. 13A, the illustrative example shows how events may be marked given initial circumstances and rule outcomes. For example, as shown at 362, when event N-2 is True and no rule set (FIGS. 12A-12B) is satisfied, then N-2 remains True and N-1 is newly marked as True. Another circumstance is shown at 364, which begins with N-2 marked as True. In this circumstance, a rule has been met, a morphology template is available to the system, and the correlation of event N-1 to the morphology template is better (higher CWA score in the illustrative example) than the correlation of event N-2 to the morphology template. In such a circumstance 364, event N-2 has its marker changed from True to False, while event N-1 is marked True. As illustrated by the circumstance at 364, the marking of an event as True is sometimes only a preliminary determination which may be changed later in the analysis.

Next, as shown at 366, in any other circumstance in which event N-2 starts True and a rule set is met, the result will be a marker of True for event N-2 and a marker of False for event N-1. Finally, as shown at 368, if the initial circumstance is that N-2 has been marked False, then event N-1 is marked True without consideration of the outcome of the application of the rule sets of FIGS. 12A-12B.

Referring to FIG. 13B, illustrative handling of True-False markers is shown. The handling relies, in part, upon the status of the system as shown at 380 and 390. A "Pattern Found" or "No Pattern" state results from identification of a detection pattern that indicates wide complex overdetection. Illustrative examples of patterns that can be used to identify "Pattern Found" and "No Pattern" states are shown below.

As shown at 380, a first system state is one in which the calculated heart rate is in a predetermined range and a pattern has been found. When in this state, the method assigns wide complex overdetection markers to selected events. In the illustrative example, when detected events N-3, N-2 and N-1 form a True-False-True sequence, then a wide complex overdetection marker is assigned to N-2. Otherwise, as shown at 384, no wide complex overdetection marker is assigned. The use of the overdetection marker is further explained with reference to FIGS. 18-21.

As shown at 390, a second system state occurs in which the rate is in range but the system is not in a pattern found state. As shown at 392, when detected events N-3, N-2 and N-1 form a True-False-True sequence, event N-2 is assigned a suspect event marker. The use of the suspect event marker, again, is explained further with reference to FIGS. 18-21. In any other combination, no WC suspect marker is assigned, as shown at 394.

As noted at 380, 390, "Pattern Found" and "No Pattern" states are defined, therefore some illustrative pattern searching examples are shown next. Generally the approach is to identify particular features of the overall rhythm, encompassing several detected events, which indicate that a pattern of Wide Complex overdetection appears likely. When such particular features are identified, a "Pattern Found" state can be invoked, allowing events to be marked as overdetections.

A first example of a pattern that may be used to define the "Pattern Found" and "No Pattern" states has been shown above in FIG. 10 as an alternating interval pattern. Different heart rate ranges may be used for Wide Complex Overdetection Analysis and Alternating Interval analysis, as indicated in FIG. 16, below. Thus, in the illustrative example, when the rate is in the Wide Complex range and the other rules (rules 232, 236) for an alternating pattern from FIG. 10 are met, the "Pattern Found" state is entered.

Other patterns may also be used to establish a "Pattern Found" state. One example uses alternating Wide Complex Suspect (WC Suspect) event markers. An alternating pattern could be: [WC Suspect]-[Not Suspect]-[WC Suspect]-[Not Suspect]. Such a four event pattern can be sufficient to enter the Pattern Found state. In one illustrative example, only suspect markers generated by the Wide Complex Overdetection method are used to identify the alternating suspect event marking. In another example, a larger set of events is used to establish the pattern, and/or any source of suspect event markers may be relied upon to establish the pattern.

Figure 14:
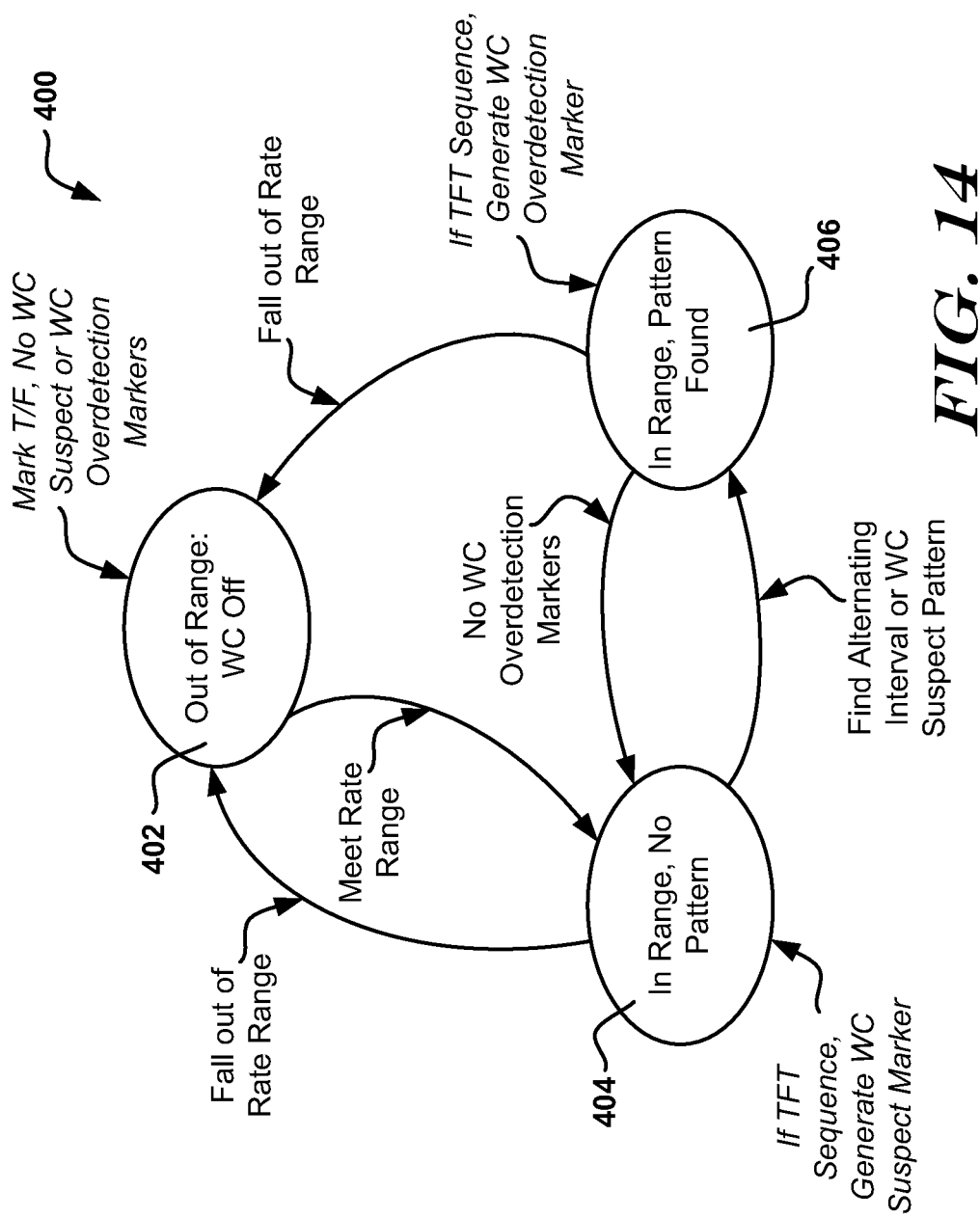
FIG. 14 is a process flow diagram for an illustrative wide complex overdetection identification method.

FIG. 14 graphically illustrates transitions between system states. The example in FIG. 14 includes two in-range states and an out of range state. In each state, the system performs True-False marking as set out in FIG. 13A. The True-False marking may be used in later steps such as charge confirmation shown in FIG. 22.

The illustration 400 provides for an Out of Range state 402, in which wide-complex suspect and overdetection marking is off (WC Off). The Out of Range state 402 is effective when the detected heart rate falls outside of a predetermined range. When the heart rate enters the range, the system leaves the Out of Range State and enters an In Range, No Pattern State 404.

Once in the In-Range, No Pattern State 404, the system begins looking for T-F-T sequences and, if any are found, suspect event marking as shown at 390-392-394 in FIG. 13B takes place. The system also looks for patterns that indicate overdetection is occurring. This may include observing a pattern of alternating long-short intervals and/or a pattern of WC Suspect event markers. In one example, a pattern as shown in FIG. 10 is sought. Once both the rate range and a pattern are found, the system then transitions to an In-Range, Pattern Found state 406.

Once in the In-Range, Pattern Found state 406, if a T-F-T pattern is found, the system assigns a Wide Complex Overdetection marker as explained at 380-382-384 in FIG. 13B. A transition from the In-Range, Pattern Found state 406 to the In-Range, No Pattern state 404 may occur if a timeout occurs without any Wide Complex Overdetection markers being assigned. In one illustrative example, if 64 consecutive detected events pass without any wide complex overdetection markers being assigned, the pattern is considered lost and the system transitions from state 406 to state 404. Use of N=64 is merely illustrative, and other thresholds may be used.

Within the illustration 400, from either In-Range state 404, 406, if the calculated rate falls outside of the rate range, the system returns to the Out of Range state 402. In an alternative embodiment, the system may wait to begin suspect event or overdetection marking until a pattern has been found in addition to meeting the rate range. In yet another embodiment, rather than entering the In Range, No Pattern state 404 when the rate enters the predetermined range, the method may assume a pattern exists and enter the In-Range Pattern Found state 406 immediately upon meeting the rate range condition.

While in the Out Of Range state 402, an illustrative method does not perform either WC Suspect or WC Overdetection marking as shown in FIG. 13B. If desired, True/False marking may be omitted while in the Out of Range state 402. In one example, however, True/False marking is performed and may be used, upon transition into the rate range, to immediately enter the In-Range, Pattern Found state 406. In another example, True/False marking is performed at all times, and a buffer of True/False markers and event polarity indications is kept in order to provide information for use in Charge Confirmation methods shown in FIG. 22. Event width and correlation scores may be carried forward as well.

Thus, FIG. 14 provides an illustration of system operation by integrating the True-False marking and suspect and/or overdetection markers of FIGS. 13A-13B, which in turn apply the rules of FIGS. 12A-12D.

The above rules indicate that, following a False event marker, the next event is marked True (Rule 368 in FIG. 13A). However, the marking of an N-1 event as "True" is a preliminary indication. During a next iteration of the method, an event that was marked True when in the N-1 analysis slot may be marked false when it is in the N-2 analysis slot, as may occur as shown by FIG. 15.

Figure 15:
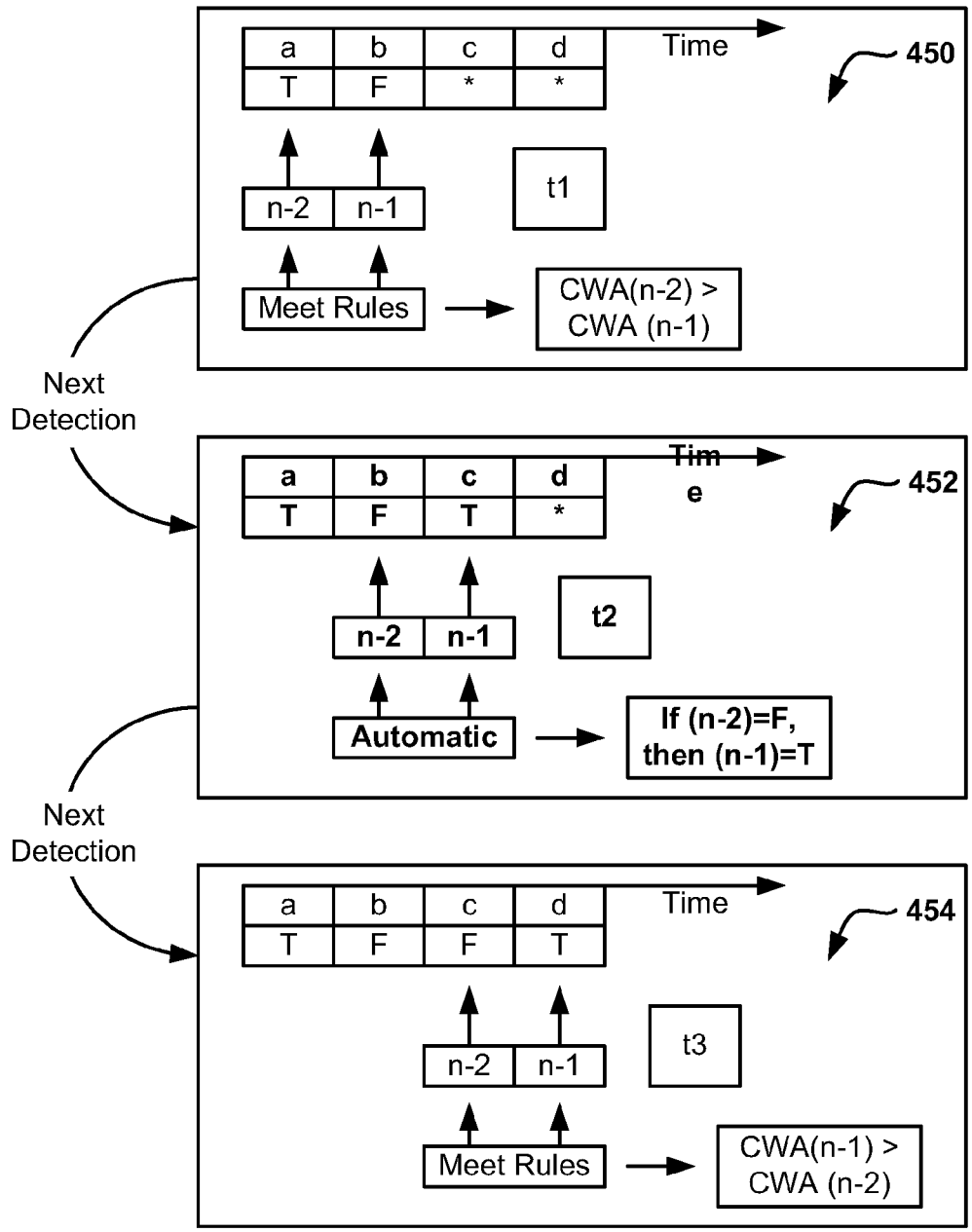
FIG. 15 provides a graphical illustration of data analysis from detection-to-detection for illustrative True-False marking.
Figure 16:
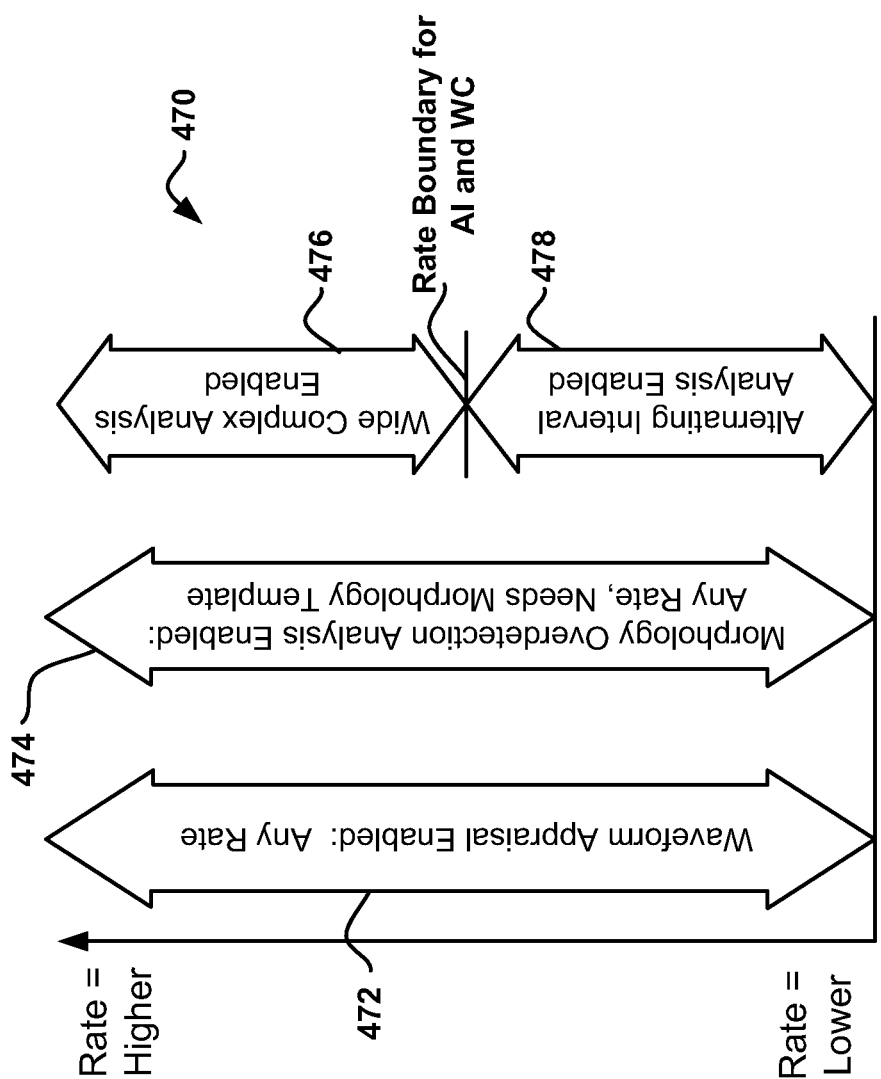
FIG. 16 shows an illustrative example for integration of a waveform appraisal method with morphology, alternating interval and wide complex overdetection methods.

FIG. 15 shows analysis of four events, a, b, c, and d, which are consecutively occurring detected events that each have passed waveform appraisal. As shown at 450, at time t1 events a and b are treated as events N-2 and N-1, respectively, for the rule analysis of FIG. 12A-12B. As shown by FIG. 13A, at 366, when the rules are met and the earlier event, N-2, does not have lesser correlation to the stored template than the latter event, N-1, the N-1 event (event b) is marked False, while the N-2 event (event a) is marked True.

The method then iterates to 452, where, at time t2, events b and c are treated as N-2 and N-1, respectively, and the rules would again be applied. Here, because event b is already marked as False, event c is automatically marked as True based on the rule shown in FIG. 13A at 368. If a Wide Complex rate range is met, the T-F-T pattern will result in the N-2 event (event b) being marked as either a Wide Complex Overdetection or as Wide Complex Suspect, depending on whether a Pattern Found state is in effect. The method next iterates to 454.

As shown at 454, events c and d are treated as N-2 and N-1, respectively, and the rules of FIG. 12A-12B are applied. As indicated, one of the rule sets of FIGS. 12A-12B is again met. In the illustrative embodiment, the correlation to the stored morphology template of the latter event, N-1, is greater than the correlation of the earlier event, N-2. As per rule 366 in FIG. 13A, the N-2 event is marked False and the N-1 event is marked True. The result of this analysis is the marking of consecutive events b and c as False. Note that at this point, an F-F-T pattern has developed. No Wide Complex Overdetection or Wide Complex Suspect event marker is applied to the N-2 event (event c), since this pattern is not one of the marker patterns shown in FIG. 13B. The consecutive False markers do, however, reduce confidence in event detection accuracy. FIG. 22, below, provides further illustration of marking and analysis for charge confirmation that can add persistence factors to therapy decisions when too many events are marked False. In yet another embodiment, if desired, a pairing of F-F may be analyzed to determine whether the two detections indicate a triple-detection pattern has occurred. For example, consecutive False markers may result in a calling of a morphology analysis to determine whether an immediately preceding or following event matches a stored or dynamic template. Alternatively, if a T-F-F-T sequence is identified, the two detections marked as True may be compared one to another; high correlation may indicate triple detection has caused the intervening False events.

Integration, Data Correction And Charge Confirmation

FIG. 16 graphically illustrates an integration of several overdetection analysis methods. In the illustrative example 470, waveform appraisal 472 may be enabled at any detected event rate, as is Morphology Overdetection Analysis 474, if a template can be established for use in the analysis.

As shown at 476, Wide Complex Overdetection Identification Analysis is enabled in a relatively higher rate zone, with Alternating Interval Overdetection Identification Analysis enabled in a lower rate zone at 478. In some embodiments, an upper limit is placed on the Wide Complex Analysis 476, for example, in the range of 405 bpm calculated heart rate, and the border between the Wide Complex Analysis 476 and Alternating Interval Analysis 478 is set in the range of about 160 bpm.

These variables may change or may be omitted. The upper and/or lower rate limits on Wide Complex Analysis 476 may be omitted, for example, as well as the upper limit on Alternating Interval Analysis 478. Also, rather than a strict "border," these analysis zones may overlap. Transitions may also take into account various hysteresis factors such as, but not limited to, crossing the "border" by an amount greater than some value (i.e. 20 ms or 20 bpm beyond the border) and/or meeting the requirement for a selected number of consecutive detected events.

FIG. 17 illustrates the use of a refined detection profile. The purpose of FIG. 17 is to show that, for any given profile, it is likely possible to identify an implantee in whom the profile may result in overdetection. The illustrative profile is similar to one of those shown in U.S. Provisional Patent Application No. 61/034,938, entitled ACCURATE CARDIAC EVENT DETECTION IN AN IMPLANTABLE CARDIAC STIMULUS DEVICE, filed on Mar. 7, 2008. As shown above the label "Overdetecting T-Waves" cardiac cycles shown at 510, 512 are double counted as both the R-waves and the trailing T-waves lead to detections. Further, as shown above the label "Overdetecting Wide Complexes," the profile also double detects the QRS complexes shown at 520, 522. Refining the detection profile may not avoid all overdetection.

FIGS. 18-21 provide illustrations of the handling of Overdetection and Suspect event markers from the above illustrative examples. FIG. 18 provides an example of what happens during "normal" detection, when no events are marked as suspect or overdetections. A buffer of detections and associated intervals is shown at 600. The definition of detection and interval is indicated at 602: a detection threshold crossing is a detection, and an interval is the period of time between consecutive detections.

As shown at 600, detections and intervals occur in an ongoing series, with a most recent detection shown at 604, separated by a most recent interval 606 from a second most recent detection 608. For illustrative purposes, the examples in FIGS. 18-21 operate using a delay of at least one event; a real time system that analyzes event 602 as soon as it is defined could be used instead.

As shown at 610, an analysis window is defined to perform analysis on three detected events and associated intervals. As the analysis 610 is completed, detected events are marked as certified detected events 612. In addition, an interval is marked as a certified interval if no suspect event or overdetection markers are applied to events defining the interval. The newest certified interval is introduced into a first-in, first-out (FIFO) buffer of certified intervals 614, as indicated by line 616.

In the illustrative example, four certified intervals 614 are used in the FIFO buffer to calculate a 4RR Average 618, which is used to find a calculated heart rate 620 for the system. In the illustrative example, until intervals are certified, they are not used in rate calculations. The analysis 610 will "certify" intervals for use in rate calculation unless the interval is marked suspect or is combined as a result of a detection being marked as an overdetection. The analysis 610 may include any of the above analyses such as waveform appraisal, morphology overdetection analysis, alternating interval overdetection analysis, and/or wide complex overdetection analysis.

Figure 19:
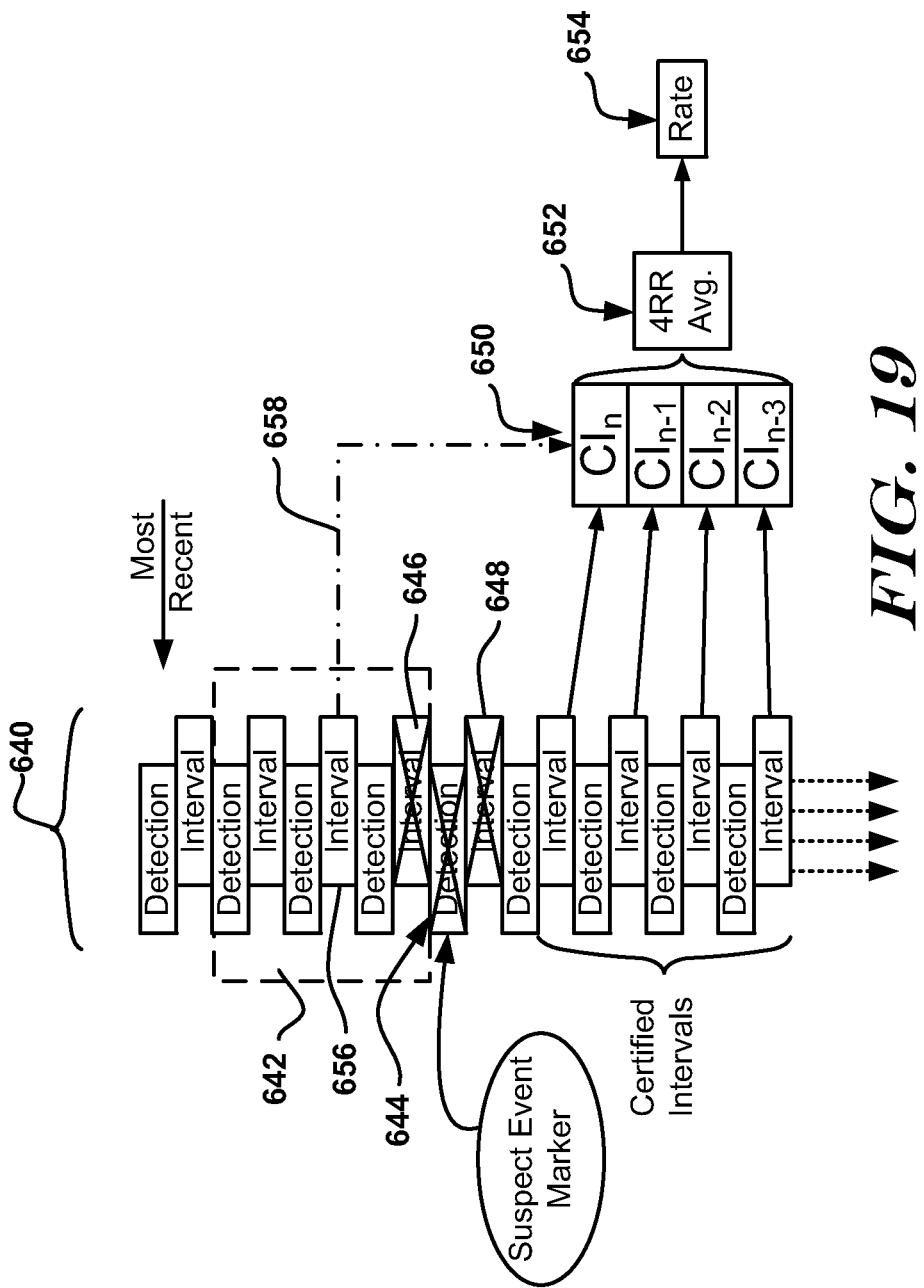

FIG. 19 shows analysis when a suspect event marker is applied. A suspect event marker is shown in the above examples as a possible outcome of Waveform Appraisal analysis or Wide Complex Overdetection Identification analysis. Within the series of detections and intervals 640, the analysis window is shown at 642. An event at 644 is marked as a suspect event.

In operation, the suspect event 644 is known to be unreliable, but it is not known whether the suspect event 644 is, for example, an R-wave masked by spurious noise, a double detection, or a detection caused by external noise. Since the source of event 644 is unclear, as indicated by its marking as suspect, each interval defined by the event 644, including both intervals 646 and 648, is determined to be unreliable for rate calculation. The method does not pass intervals 646, 648 to the buffer of certified intervals 650 which is used to generate the 4RR average 652 and hence the rate 654. Instead, prior intervals that have already been certified are retained in the buffer 650 until a new interval is certified. For example, if neither of the detections on either side of interval 656 are marked as suspect or as overdetections, then interval 656 will pass to the buffer 650 once analysis 642 has moved on, as indicated by 658.

Figure 20:
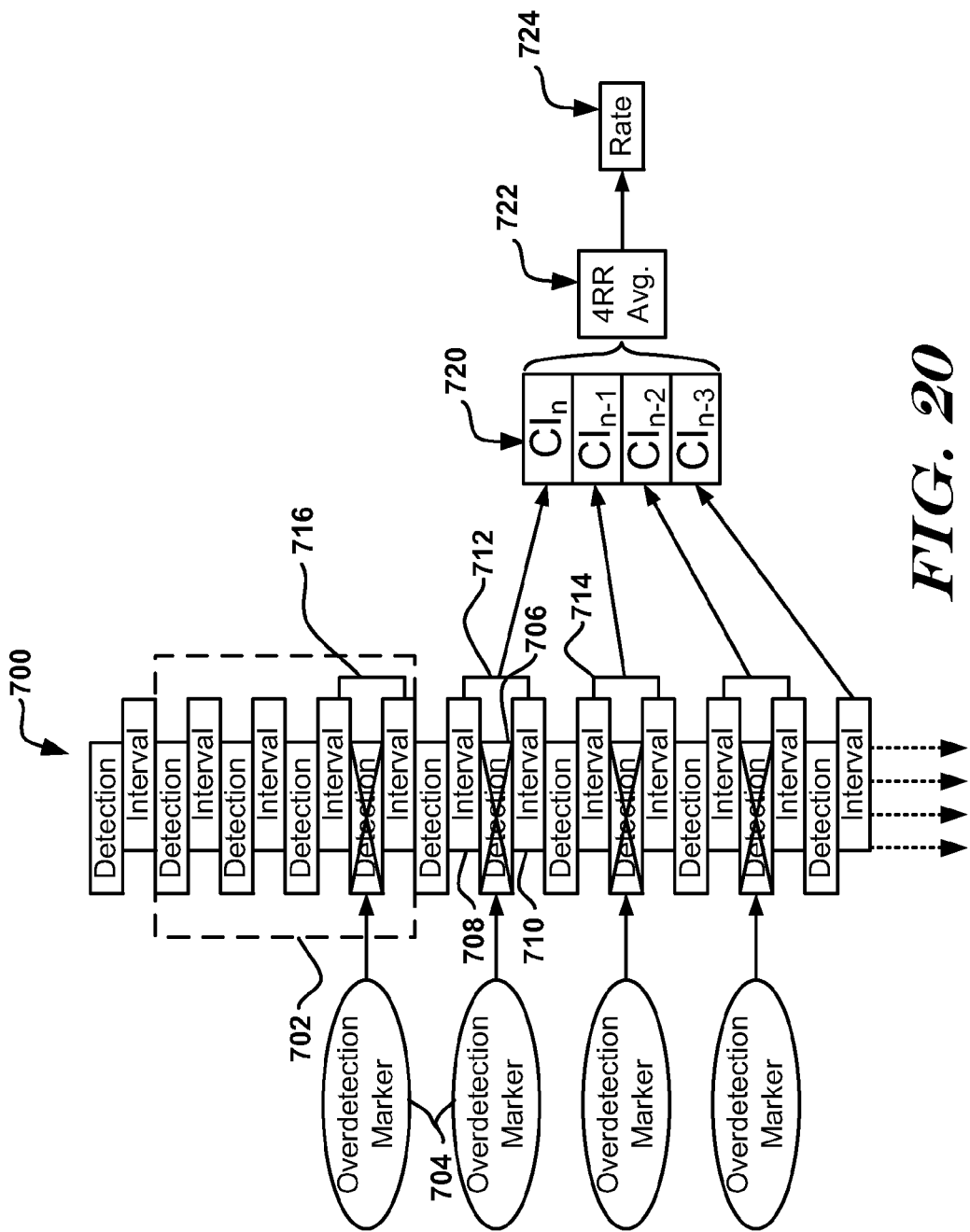

FIG. 20 shows treatment of overdetection markers. In the example shown, persistent overdetection is marked within the series of detections and intervals 700. The analysis window is shown at 702, and overdetection markers are shown at 704. In the illustrative example, data is corrected when an overdetection marker is applied. More specifically, intervals around an event having an overdetection marker are combined, and the event itself is discarded.

For example, an overdetection marker is applied to the detection at 706. The intervals 708, 710 on either side of detection 706 are combined into a single interval 712. Detection 706 may also be discarded, for example, removing it from estimated peak calculation(s). This combined interval 712 is brought into the certified interval buffer 720. Likewise, a combined interval at 714 enters the buffer 720. As the analysis continues, the combined interval shown at 716 will also be added to the buffer 720 and used to generate the 4RR Average 722 and rate 724.

FIG. 20 provides a contrast to FIG. 19. When a detection is marked suspect, as in FIG. 19, it is not known whether an associated cardiac cycle has been counted yet. An overdetection 706, when identified, likely corresponds to a cardiac cycle that has already been counted by another detection. Therefore, data correction by combining intervals 708, 710 into combined interval 712 is determined to be appropriate.

It should be noted that for either of FIG. 19 or FIG. 20, in addition to modifying the rate calculation, applying a suspect event or overdetection marker may also change the calculation of an estimated peak. As noted, overdetections or suspect events may sometimes lower the estimated peak and increase the likelihood of further overdetection. When a suspect event or overdetection marker is applied, some embodiments exclude one or more detected events from calculation of the estimated peak. In one illustrative example, if two previous peaks would usually be averaged to calculate estimated peak, if an overdetection or suspect event marker is applied, the larger peak of the two peaks may be used as the estimated peak.

Figure 21:
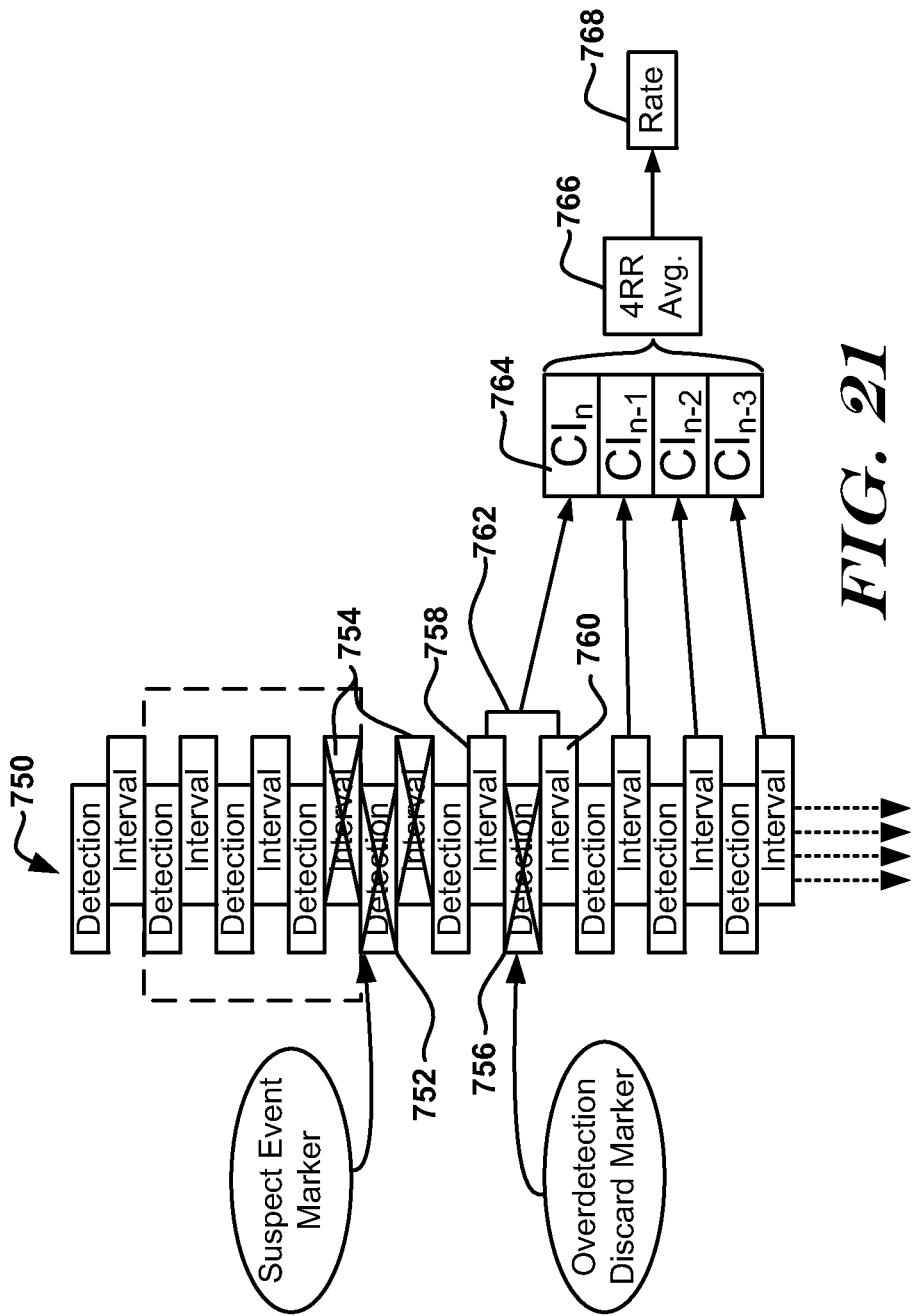

FIG. 21 combines the above analysis of FIGS. 19-20 by showing a circumstance in which both suspect event and overdetection markers are applied. In the data 750, a suspect event marker has been applied at 752. This results in intervals shown at 754 being marked as suspect and treated as unreliable and unusable.

Also in FIG. 21, the detection at 756 is marked as an overdetection. This detection 756 is then discarded and the associated intervals 758, 760 are combined into a single interval 762. The combined interval 762 is used in the buffer of certified intervals 764, which is used to calculate the 4RR Average 766 and heart rate 768.

FIG. 22 provides an example of charge confirmation analysis. The method of FIG. 22 is largely directed toward analyzing whether therapy is proper at a time when the cardiac rhythm is likely malignant. The analysis of FIG. 22 is largely an effort to avoid improper therapy delivery to an implantee when overdetection is occurring. The method in FIG. 22 may be performed as part of a therapy decision, for example, as shown at 22 in FIG. 1 or 48 in FIG. 2. The analysis shown in FIG. 22 includes a Start Block which would begin with an internal variable, denoted "Tolerance" in the Figure, is initialized to zero, and the Start Block would be called once other factors (such as the X/Y and persistence conditions noted above) are already met.

FIG. 22 makes use of two further data sets. First, individual events are tagged as 0, 1 or 2 using the True-False and polarity designations from FIGS. 12A-12D and 13A, as follows:

If marked True, the event receives tag 0.

If marked False and having positive polarity, the event receives tag 1.

If marked False and having negative polarity, the event receives tag 2.

Several counters are then generated from a buffer of the 16 most recent detected events that have passed waveform appraisal (this would include events marked as overdetections and/or suspect by methods other than waveform appraisal), as follows:

Total_WC_Beats: Number of Wide Complex Suspect or Wide Complex Overdetection marked detections in the buffer Max_Cons_01: Maximum number of consecutive 0-1 tag combinations Max_Cons_02: Maximum number of consecutive 0-2 tag combinations These calculated variables are then used as shown in FIG. 22.

Beginning at a start block 800, the method determines if Total_WC_Beats is less than six, as shown at 802. If not, the method checks whether Total_WC_Beats is greater than or equal to eight, as shown at 804. If so, the method determines whether Max_Cons_01 is greater than or equal to three, as shown at 806. If not, the method determines whether Max_Cons_02 is greater than or equal to three, as shown at 808. If not, the variable "Tolerance," which is an integer variable created for use as a persistence factor in the flow diagram of FIG. 22, is compared to five. If Tolerance is greater than or equal to five, as shown at 810, the charge confirmation method is satisfied, and the method returns an indication to start charging, as shown at 812, for the purpose of charging high power capacitors for use in delivering therapy.

Going back to step 810, if Tolerance is not equal to or greater than five, the method goes to block 814, where Tolerance is incremented and the method returns an indication that charging should not be started, as indicated at 816. Setting the Tolerance limit as five is merely illustrative, and larger or smaller settings may be used.

Continuing back through the method to capture alternative outcomes, if either of blocks 806 or 808 returns a Yes result, then the method resets the Tolerance variable to zero, as shown at 818, and the method returns an indication that charging should not be started, as shown at 816. The consecutive pairings of 0-1 or 0-2 that trigger reset of the Tolerance variable from blocks 810 and/or 812 indicates repetitive double detections having similar morphology over time. Resetting the Tolerance variable is allowed in each of these circumstances at least because a requisite level of polymorphic behavior that would be associated with ventricular fibrillation and/or highly discordant arrhythmias (such as polymorphic ventricular tachycardia) is not occurring. Such judgments regarding the cardiac rhythms that will or will not be treated aggressively may vary in some embodiments or in response to physician preference.

In some embodiments, a triple detection identification method may be called in addition to the other overdetection identification methods shown herein. The use of True-False and 0-1-2 marking shown above may provide analytical tools for such triple detection identification. In one such embodiment, triple detection patterns are identified by observing whether a pattern of 0-1-2 or 0-2-1 repeats, such as {0-1-2-0-1-2-0 ... }, and data correction to remove each of the 1 and 2 detections can be performed. Such an embodiment may include analysis of the True (0) detections to determine whether narrow QRS features can be identified.

In block 802, the Yes result likely indicates a shockable rhythm such as ventricular fibrillation. Therefore, the method goes directly to block 816 and returns a result indicating that charging should begin. This bypass of the "Tolerance" analysis may be omitted in some embodiments. Finally, if block 804 returns a No result, then the checks at 806 and 808 are determined to be unnecessary, and the method skips to block 810 where the Tolerance variable is checked.

In an illustrative example, the charge confirmation method shown in FIG. 22 is used as a prerequisite to initiating charging of high-power capacitors in an implantable cardioverter-defibrillator or other implantable therapy delivery system. Once capacitor charging begins, in an illustrative example, the method of FIG. 22 is no longer invoked until a shock is delivered or the episode terminates.

Figure 23:
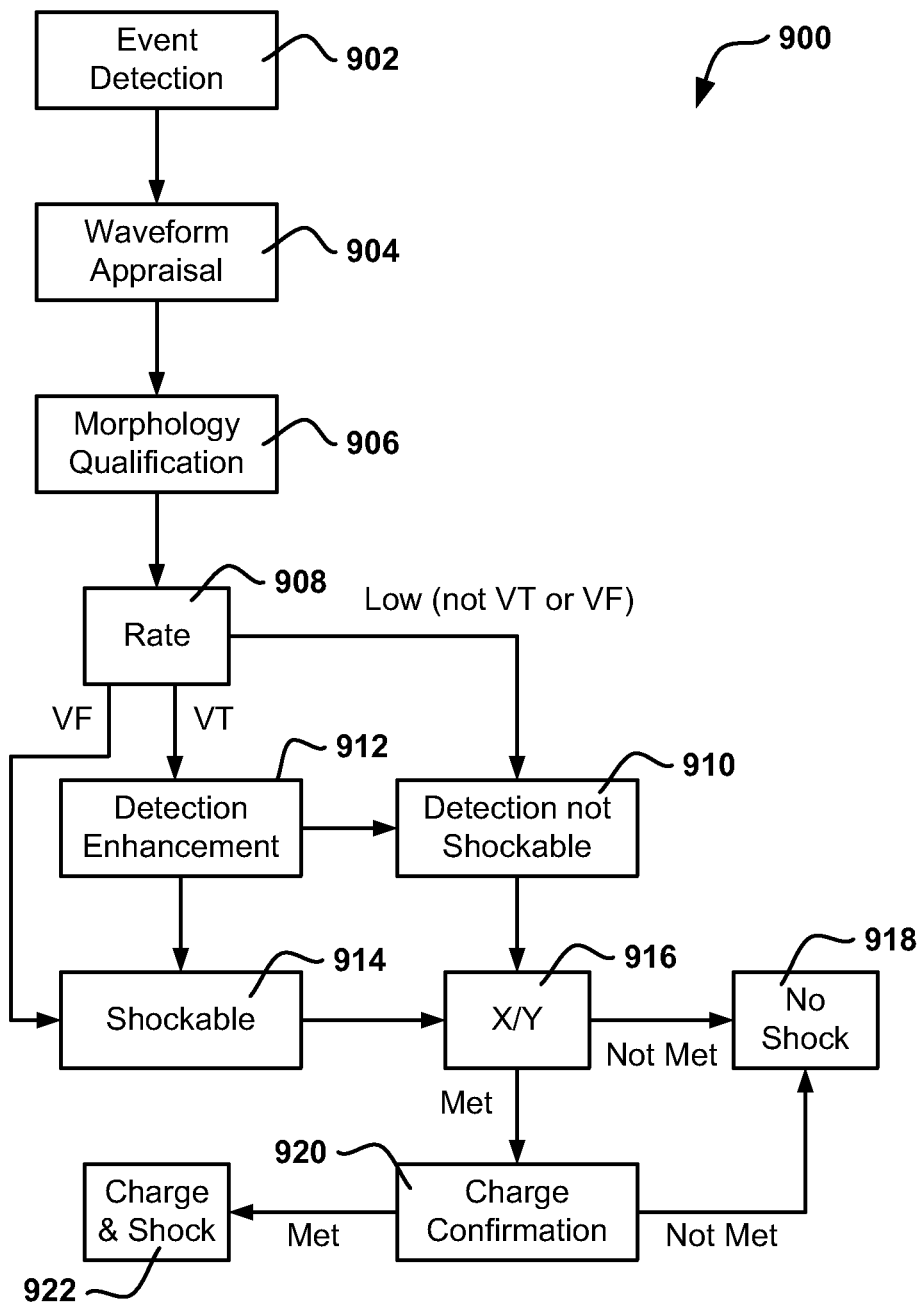
FIG. 23 shows an illustrative method of analysis.

FIG. 23 shows an example of analysis. Some analysis methods take an approach in which a series of buffers are filled during analysis toward a decision to deliver therapy to a patient. For example, cardiac rate may be measured and, once calculated as tachyarrhythmic, a counter begins to determine how many consecutive rate calculations occur having the tachyarrhythmic rate. Once the tachyarrhythmic rate counter is filled, a tachy condition is met and the device will perform additional morphology analysis to determine whether the patient is showing a monomorphic rhythm and/or whether the patient's individual detected events are not correlated to a stored template. In this example, morphology analysis occurs at the end of the analysis. By only using the morphology analysis at the end of the analysis, it is underemphasized. With morphology only at the end of the analytical method, incorrect therapy decisions may not be avoided.

In contrast, the method of FIG. 23 is shown at 900 using a different order. In particular, the method 900 follows event detection 902 with waveform appraisal 904, in which the detected event is analyzed by itself to determine whether it likely is caused by, or is masked by, noise. As suggested above, waveform appraisal 904 may take a form as shown in U.S. Pat. No. 7,248,921, titled METHOD AND DEVICES FOR PERFORMING CARDIAC WAVEFORM APPRAISAL. Next, morphology qualification takes place, as shown at 906. Morphology qualification 906 includes one or more of the double detection methods shown above, such as wide complex overdetection, morphology overdetection, and alternating interval overdetection.

Next, the rate is estimated, as shown at 908. The rate is characterized as falling into one of three zones: A VF zone, a VT zone, and a Low zone. The VF zone is a high zone, typically greater than 180 bpm, and sometimes higher than 240 bpm, for example. The Low zone is a non-malignant zone, for example, below 140 bpm, though possibly reaching to as high as 170 bpm for some patients, and even higher, particularly with younger patients. The VT zone is defined between the Low zone and the VF zone. In this example, "VT" and "VF" are simply labels, not diagnoses. The rate estimate may make use of the methods shown above that correcting data in response to identified overdetection.

If the rate is Low, the detected event is marked as not shockable, as indicated at 910. If the rate is in the VT zone, an optional detection enhancement 912 may be called. In an illustrative example, detection enhancement 912 includes a tiered analysis in which the detected event under consideration is compared to a static template. If the detected event correlates well with the static template, the detected event is marked as not shockable 910. If the event does not correlate to the static template but does correlate well to a dynamic template formed of an average of four recently captured events and shows a narrow QRS complex (the combination suggests a monomorphic tachycardia having narrow complexes), the method will also proceed to step 910. Otherwise, if detection enhancement 912 fails, the detected event is marked as shockable, as shown at 914.

If the rate calculated at 908 is in the VF zone, detection enhancement 912 may be bypassed and the detected event is marked as shockable as shown at 914. In one embodiment, the implantable device is programmed to set the boundaries of the VT zone and VF zone and/or to omit the VT zone. In yet another embodiment, the VF zone may be omitted, and all rates above the Low zone would be directed through detection enhancement 912.

The markings of shockable and not shockable are maintained in an X/Y counter, which provides an initial counter for determining whether to proceed to therapy. If the X/Y counter fails (counters such as 12/16, 18/24, or 24/32, for example, may be used), then no therapy is applied and the method of analysis ends with no shock 918. The system then waits to call the method again when the next detection occurs. The X/Y counter 916 may also integrate a persistence factor, for example, calling for the X/Y counter condition to be met for a series of consecutive detected events.

The illustrative method 900 also calls a charge confirmation check, as shown at 920. The charge confirmation check 920 may be as shown above in FIG. 22. The charge confirmation check, if passed, leads to the decision to charge and shock 922. Charge and shock 922 may be called with analysis continuing to ensure that the patient's malignant rhythm does not correct itself. If the patient's malignant rhythm returns to normal before a shock is delivered, the method may terminate the charge and shock sequence 922. If the charge confirmation check 920 does not pass, the method again ends at 918 and waits for the next detected event.

The method shown in FIG. 23 is separable from the other methods shown above for identifying overdetections and/or for correcting data resulting from overdetection.

Additional Features

Some embodiments take the form of devices and methods that are directed toward cardiac activity monitoring. One example may be an implantable loop recorder. Referring to FIG. 1, for monitoring embodiments, rather than a therapy decision 22, a decision to store certain data for later upload may be made instead. For example, some implantable monitors are configured to retain data only when a decision is made by the implant that abnormal and/or potentially malignant activity is occurring. In some further embodiments, data may be stored when captured data requires correction, in order that the sensing and detection characteristics of the system and/or implant location may be analyzed to determine its suitability for long-term use. A monitoring system may also output a warning if a malignant condition is identified, for example by annunciation to the implantee or by communication with an external alert system.

The X out of Y counter referred to above may be integrated with a persistence factor as in US Patent Application Publication Number 2006/0167503, now issued as U.S. Pat. No. 8,160,697, titled METHOD FOR ADAPTING CHARGE INITIATION FOR AN IMPLANTABLE CARDIO-VERTER-DEFIBRILLATOR. A persistence factor requires the X out of Y counter requirement be met for a predetermined number of consecutive iterations. In the illustrative example, the charge confirmation method of FIG. 22 is integrated as an additional requirement that follows the persistence factor. That is, in the illustrative example, charge confirmation would be invoked only after the persistence requirement is satisfied by meeting the X out of Y counter requirement for a predetermined number of consecutive iterations. If/when a non-sustained arrhythmic condition is identified, the persistence factor and/or X/Y condition may be modified as explained in the 2006/0167503 publication.

The above illustrative examples may be embodied in many suitable forms. Some embodiments will be method embodiments incorporating one or more of the above features/sub-methods in various combinations. Some embodiments will be devices adapted to perform one or more of the methods discussed above and/or a system including implantable devices and associated external programming devices. Some embodiments will take the form of tangible media, such as magnetic, electric, or optical storage media, incorporating controller readable instruction sets. Some embodiments will take the form of or comprise controllers/microcontrollers associated with stored instruction sets for directing operations of various components in a device in accordance with one or more methods.

The design details of operational circuitry contained within a canister, such as canister 62 in FIG. 3, may vary widely. Briefly, an illustrative example may make use of a microcontroller-driven system which includes an input switch matrix for selecting one or more signal vectors as a sensing vector. The switch matrix is coupled to filtering circuitry and at least one input amplifier. The amplified, filtered signal is typically fed to analog-to-digital conversion circuitry. Additional filtering of the incoming signal may be performed in the digital domain including, for example, 50/60 Hz notch filters. The incoming signal may then be analyzed using the microcontroller and any associated suitable registers and logic circuits. Some embodiments include, for example, dedicated hardware for peak or event detection and measurement, or for morpohology analysis such as correlation waveform analysis or wavelet transform analysis.

In several illustrative examples, upon identification of a rhythm that indicates therapy, a charging operation is undertaken to charge one or more capacitors to suitable levels for therapy. A charging sub-circuit may take any suitable form. One example uses a flyback transformer circuit, a structure well known in the art. Any process and/or circuit that enables relatively low voltage batteries to charge capacitors to relatively high voltages may be used. Some systems also perform annunciation and/or communication in response to detected malignancy, for example, to alert the implantee or a medical facility that therapy is imminent or intervention is needed.

The device may further include output circuitry comprising, for example, an output H-bridge or modification thereof for controlling output polarity and pulse duration from the high-power capacitor. Control circuitry associated with the H-bridge may be included, for example, to monitor or control current levels for constant current output signals or for performing diagnostic functions.

The circuitry may be housed in a hermetically sealed canister made of any suitable material.

The above description details several over-detection identification methods and associated data correction methods. Each of these methods may be used individually in some embodiments. For example, the wide-complex overdetection identification methods shown below may be used as a stand-alone method for identifying and, if desired, correcting overdetection. In some embodiments, multiple methods are used in a synchronized manner, for example, each of a morphology overdetection, alternating interval, and wide-complex overdetection methods may be used together and may analyze individual detected events or groups of detected events continuously. In yet other embodiments, a combination of these methods is used in response to given conditions.

In addition to selective activation of the separate over-detection analysis methods, there are several ways to integrate the results of over-detection analysis in addition to those shown by FIGS. 18-21. The following summaries provide alternatives and variants upon the illustrative examples shown above. In one illustrative example, the outcomes are integrated as follows:
  1. Waveform Appraisal suspect events can be used in Over-detection Analysis. Any event marked as an Overdetection by any method is discarded with associated interval correction, regardless of any Suspect marker;
  2. Any event marked Suspect by any method and not marked Overdetection by any method is Suspect; and
  3. Any event not marked Overdetection or Suspect is considered certified once it is no longer eligible to be marked Overdetection or Suspect.

This example allows detected events that fail waveform appraisal to be used in later identification of overdetection.

Some examples do not allow detected events that fail waveform appraisal to be used in any subsequent analysis. Thus, in another illustrative example, the outcomes are integrated as follows:
  1. Any Waveform Appraisal Marking of a Suspect event prevents marking of that event by any other method, and that event and associated intervals are marked WA Suspect;
  2. Any event marked Overdetection and not WA Suspect is discarded with associated interval correction, regardless of any Suspect marker;
  3. Any event marked Suspect by any method other than Waveform Appraisal is Suspect unless it was marked Overdetection by any method; and
  4. Any event not marked Overdetection or Suspect is considered certified once it is no longer eligible to be marked Overdetection or Suspect.

In some embodiments, marking of a detected event as suspect in waveform appraisal disables classification of adjacent events by overdetection methods. This prevents a likely noise detection from causing an actual detection to be discarded. Certain counters may be preserved to avoid impact by the WA Suspect event as well, for example, when identifying a pattern for Alternating Interval Overdetection identification (or to enable the Pattern Found state of the Wide Complex Overdetection methods), one may exclude WA suspect events and one or more adjacent events, if desired.

While voltage and power levels may vary, in one example, an implantable subcutaneous cardioverter-defibrillator includes charging circuitry and capacitors sized to receive and hold energy at 1350 volts, and uses output circuitry/controller that provide an output that yields a delivered charge of 80 Joules in a biphasic waveform with about 50% tilt. Other voltage, energy and tilt levels (higher and/or lower), and other waveforms may be used, and the load varies in response to electrode position and physiology. The configuration of output waveform need not be static, and any suitable methods/configurations for providing the output may be used (including, without limitation, pre-shock waveforms, monophasic or multiphasic waveforms, adaptation or progression of therapy energy or voltage level, changes in duration or polarity, fixed current or fixed voltage, etc.) Some embodiments use tiered therapies including anti-tachycardia-pacing as well as cardioversion and/or defibrillation stimuli. The above generally assumes two output electrodes (an anode and a cathode), however, it is understood that other systems including, for example, arrays, and/or three or more electrode stimulus systems may be used in which a pair or more electrodes are used in common.

Analysis may take several forms in terms of the inputs taken. For example, a multiple sensing electrode system may be configured to select a default sensing vector and use the default vector throughout analysis. Other systems may prioritize vectors for use in tiered analysis in which one vector is analyzed after another. Yet other systems may analyze multiple vectors simultaneously.

For purposes of conversion into the digital domain, any suitable sampling frequency may be used. Some examples use 256 Hertz; other frequencies may be used as desired. Further, the illustrative examples shown with respect to particular values can be varied, including, without limitation, changes to the refractory periods, event and peak proximity periods, rate ranges, "shockable" event rates, the number of intervals used to estimate rate, and any other values provided. Analysis using "suspect" or "certified" events and intervals, waveform appraisal, and other features may vary, and some of these features may be omitted in some embodiments. The completeness of the examples shown is not an indication that all parts are necessary to any given embodiment.

Those skilled in the art will recognize that the present invention may be manifested in a variety of forms other than the specific embodiments described and contemplated herein. Accordingly, departures in form and detail may be made without departing from the scope and spirit of the present invention.

What is claimed is:

1. An implantable cardiac stimulus device (ICSD) comprising a canister housing operational circuitry and a lead electrode assembly including a plurality of electrodes disposed thereon, with the lead electrode assembly configured to couple to the canister to electrically couple the operational circuitry to the electrodes on the lead electrode assembly, the operational circuitry being configured to perform a method of cardiac signal analysis comprising:
the operational circuitry detecting a series of events;
the operational circuitry identifying intervals between consecutive detected events;
the operational circuitry marking individual detected events as either True or False based upon a set of rules directed at identifying overdetections;
the operational circuitry determining whether a pattern of overdetection has been identified and:
a) if so, the operational circuitry discarding detected events marked as False and the operational circuitry combining intervals on either side of discarded events into combined intervals; or
b) if not, the operational circuitry marking False detected events as suspect;
the operational circuitry performing rate analysis using combined intervals, if any, and intervals between consecutive true events, but not using intervals immediately before and after suspect events, if any; and
the operational circuitry using the rate analysis to determine whether a high cardiac rate condition needing therapy is likely occurring.

2. The ICSD of claim 1 wherein the operational circuitry is further configured to also determine whether a malignant cardiac rhythm is occurring and, if so, to deliver electrical therapy in response to the malignant cardiac rhythm.

3. The ICSD of claim 1 wherein the operational circuitry is further configured such that the step of determining whether a pattern of overdetection has been identified includes:
the operational circuitry observing whether a pattern of alternating long-short intervals appear between detected events; and
the operational circuitry observing whether a pattern of alternating True-False markings occurs;
wherein if either the pattern of alternating long-short intervals or the pattern of alternating True-False markings is found, a pattern of overdetection is identified.

4. The ICSD of claim 1 wherein the operational circuitry is further configured to determine whether any of the detected events results from or is masked by noise, wherein the operational circuitry is also configured to mark as suspect any detected events resulting from or masked by noise, as well as the intervals immediately before and after such events.

5. The ICSD of claim 4 wherein:
the operational circuitry is configured to perform correlation analysis of a detected event by comparing a detected event to a template; and
the set of rules directed at identifying overdetections includes a rule for identifying an overdetection indicated by a set of detected events in which an alternating pattern of correlation occurs.

6. The ICSD of claim 4 wherein the set of rules directed at identifying overdetections includes a rule for identifying an overdetection indicated by a set of detected events in which the intervals between detected events alternate between long and short intervals.

7. The ICSD of claim 1 wherein:
the operational circuitry is configured to perform correlation analysis of a detected event by comparing a detected event to a template; and
the set of rules directed at identifying overdetections includes a rule for identifying an overdetection indicated by a set of detected events in which an alternating pattern of correlation occurs.

8. The ICSD of claim 1 wherein the set of rules directed at identifying overdetections includes a rule for identifying an overdetection indicated by a set of detected events in which the intervals between detected events alternate between long and short intervals.

9. The ICSD of claim 1 wherein the set of rules directed at identifying overdetections includes a rule for identifying an overdetection indicated by a set of detected events in which a pair of detected events are assessed for close proximity in time and alternating shape features.

10. The ICSD of claim 1 wherein the set of rules directed at identifying overdetections includes a rule for identifying an overdetection indicated by a set of detected events in which a pair of detected events are assessed for close proximity in time and peaks within the pair of detected events are also assessed for close proximity in time.

11. A method of operating an implantable cardiac stimulus device (ICSD);
wherein the ICSD comprises a canister housing operational circuitry and a plurality of electrodes coupled to the operational circuitry for sensing cardiac signals;
the method comprising the operational circuitry performing an analysis by receiving signals from the electrodes and:
detecting a series of events;
identifying intervals between consecutive detected events;
marking individual detected events as either True or False based upon a set of rules directed at identifying overdetections;
determining whether a pattern of overdetection has been identified and:

a) if so, discarding detected events marked as False and the operational circuitry combining intervals on either side of discarded events into combined intervals; or b) if not, marking False detected events as suspect;

performing rate analysis using combined intervals, if any, and intervals between consecutive true events, but not using intervals immediately before and after suspect events, if any; and using the rate analysis to determine whether a high cardiac rate condition needing therapy is likely occurring.

12. The method of claim 11 further comprising the operational circuitry:

determining whether a malignant cardiac rhythm is occurring and, if so, delivering electrical therapy in response to the malignant cardiac rhythm.

13. The method of claim 11 wherein such that the step of determining whether a pattern of overdetection has been identified includes the operational circuitry:

observing whether a pattern of alternating long-short intervals appear between detected events; and observing whether a pattern of alternating True-False markings occurs;

wherein the method includes the operational circuitry identifying a pattern of overdetection if either the pattern of alternating long-short intervals or the pattern of alternating True-False markings is found.

14. The method of claim 11 further comprising the operational circuitry:

determining whether any of the detected events results from or is masked by noise; and marking as suspect any detected events resulting from or masked by noise, as well as the intervals immediately before and after such events.

15. The method of claim 14 wherein the set of rules for identifying overdetection includes an alternating correlation rule, and the method further comprises the operational circuitry:

performing correlation analysis of a detected event by comparing a detected event to a template; and identifying an overdetection indicated by a set of detected events in which an alternating pattern of correlation occurs.

16. The method of claim 14 wherein the set of rules directed at identifying overdetections includes a rule for identifying an overdetection indicated by a set of detected events in which the intervals between detected events alternate between long and short intervals; and the method further comprises the operational circuitry identifying an overdetection by identifying a set of detected events having a prescribed pattern of alternating long and short intervals.

17. The method of claim 11 wherein the set of rules for identifying overdetection includes an alternating correlation rule, and the method further comprises the operational circuitry:

performing correlation analysis of a detected event by comparing a detected event to a template; and identifying an overdetection indicated by a set of detected events in which an alternating pattern of correlation occurs.

18. The method of claim 11 wherein the set of rules directed at identifying overdetections includes a rule for identifying an overdetection indicated by a set of detected events in which the intervals between detected events alternate between long and short intervals; and the method further comprises the operational circuitry identifying an overdetection by identifying a set of detected events having a prescribed pattern of alternating long and short intervals.

19. The method of claim 11 wherein the set of rules directed at identifying overdetections includes a wide complex rule for identifying an overdetection indicated by a set of detected events in which a pair of detected events are assessed for close proximity in time and alternating shape features; and the method further comprises the operational circuitry identifying an overdetection by using the wide complex rule.

20. The method of claim 11 wherein the set of rules directed at identifying overdetections includes a wide complex rule for identifying an overdetection indicated by a set of detected events in which a pair of detected events are assessed for close proximity in time and peaks within the pair of detected events are also assessed for close proximity in time; and the method further comprises the operational circuitry identifying an overdetection by using the wide complex rule.

* * * * *